US009863857B2

(12) United States Patent
Su et al.

(10) Patent No.: US 9,863,857 B2
(45) Date of Patent: *Jan. 9, 2018

(54) DEVICE AND METHOD FOR PARTICLE COMPLEX HANDLING

(71) Applicant: INTEL CORPORATION, Santa Clara, CA (US)

(72) Inventors: Xing Su, Cupertino, CA (US); David J. Liu, Fremont, CA (US); Kai Wu, Mountain View, CA (US); Kenneth B. Swartz, Mountain View, CA (US); Mineo Yamakawa, Campbell, CA (US)

(73) Assignee: Intel Corporation, Santa Clara, CA (US)

( * ) Notice: Subject to any disclaimer, the term of this patent is extended or adjusted under 35 U.S.C. 154(b) by 315 days.

This patent is subject to a terminal disclaimer.

(21) Appl. No.: 14/448,141

(22) Filed: Jul. 31, 2014

(65) Prior Publication Data

US 2014/0342470 A1 Nov. 20, 2014

Related U.S. Application Data

(60) Continuation of application No. 13/430,171, filed on Mar. 26, 2012, now Pat. No. 8,795,523, which is a
(Continued)

(51) Int. Cl.
*G01N 1/40* (2006.01)
*G01N 35/08* (2006.01)
(Continued)

(52) U.S. Cl.
CPC ...... *G01N 1/4044* (2013.01); *B01L 3/502761* (2013.01); *B01L 3/502784* (2013.01);
(Continued)

(58) Field of Classification Search
CPC .. G01N 1/4044; G01N 35/08; G01N 35/0098; B01L 3/502784; B01L 3/502761;
(Continued)

(56) References Cited

U.S. PATENT DOCUMENTS 6,632,655 B1   10/2003   Mehta et al.
7,442,339 B2   10/2008   Sundararajan et al.
(Continued)

FOREIGN PATENT DOCUMENTS

DE     WO 9949319 A1 *   9/1999   .......... B01J 19/0093

*Primary Examiner* — David A Reifsnyder
(74) *Attorney, Agent, or Firm* — Schwegman Lundberg & Woessner, P.A.

(57) ABSTRACT

An embodiment of the invention relates to a device for detecting an analyte in a sample. The device comprises a fluidic network and an integrated circuitry component. The fluidic network comprises a sample zone, a cleaning zone and a detection zone. The fluidic network contains a magnetic particle and/or a signal particle. A sample containing an analyte is introduced, and the analyte interacts with the magnetic particle and/or the signal particle through affinity agents. A microcoil array or a mechanically movable permanent magnet is functionally coupled to the fluidic network, which are activatable to generate a magnetic field within a portion of the fluidic network, and move the magnetic particle from the sample zone to the detection zone. A detection element is present which detects optical or electrical signals from the signal particle, thus indicating the presence of the analyte.

10 Claims, 16 Drawing Sheets

Related U.S. Application Data division of application No. 13/197,918, filed on Aug. 4, 2011, now Pat. No. 8,158,008, which is a division of application No. 11/647,566, filed on Dec. 29, 2006, now Pat. No. 7,993,525.

(51) Int. Cl.

| | | |
|---|---|---|
| *B01L 3/00* | (2006.01) | |
| *G01N 35/00* | (2006.01) | |
| *G01N 15/00* | (2006.01) | |
| *H01F 7/20* | (2006.01) | |
| *H01F 7/06* | (2006.01) | |

(52) U.S. Cl.
CPC ...... *G01N 35/08* (2013.01); *B01L 2200/0647* (2013.01); *B01L 2200/0673* (2013.01); *B01L 2300/0816* (2013.01); *B01L 2400/043* (2013.01); *B01L 2400/0424* (2013.01); *B01L 2400/0638* (2013.01); *B01L 2400/086* (2013.01); *G01N 35/0098* (2013.01); *G01N 2015/0038* (2013.01); *G01N 2015/0092* (2013.01); *H01F 7/20* (2013.01); *H01F 7/206* (2013.01); *H01F 2007/068* (2013.01); *Y10S 436/805* (2013.01); *Y10S 436/806* (2013.01); *Y10T 29/4913* (2015.01); *Y10T 29/49117* (2015.01); *Y10T 29/49155* (2015.01); *Y10T 436/25* (2015.01)

(58) Field of Classification Search
CPC ..... B01L 2400/0638; B01L 2200/0673; B01L 2400/086; B01L 2400/043; B01L 2200/0647; B01L 2400/0424; Y10T 436/25; Y10S 436/806

See application file for complete search history.

(56) References Cited

U.S. PATENT DOCUMENTS

| | | | |
|---|---|---|---|
| 7,820,454 B2 | 10/2010 | Su et al. | |
| 7,993,525 B2 | 8/2011 | Su et al. | |
| 8,158,008 B2* | 4/2012 | Su | G01N 35/08 210/222 |
| 8,409,877 B2 | 4/2013 | Liu et al. | |
| 8,586,385 B2* | 11/2013 | Su | B01L 3/502761 435/7.1 |
| 8,795,523 B2* | 8/2014 | Su | G01N 1/4044 210/222 |
| 2003/0012693 A1 | 1/2003 | Otillar et al. | |
| 2005/0284817 A1 | 12/2005 | Fernandez et al. | |
| 2007/0248497 A1 | 10/2007 | Robillot | |
| 2008/0160630 A1 | 7/2008 | Liu et al. | |
| 2008/0160634 A1 | 7/2008 | Su et al. | |
| 2011/0065140 A1 | 3/2011 | Su et al. | |
| 2012/0035084 A1 | 2/2012 | Su et al. | |

* cited by examiner

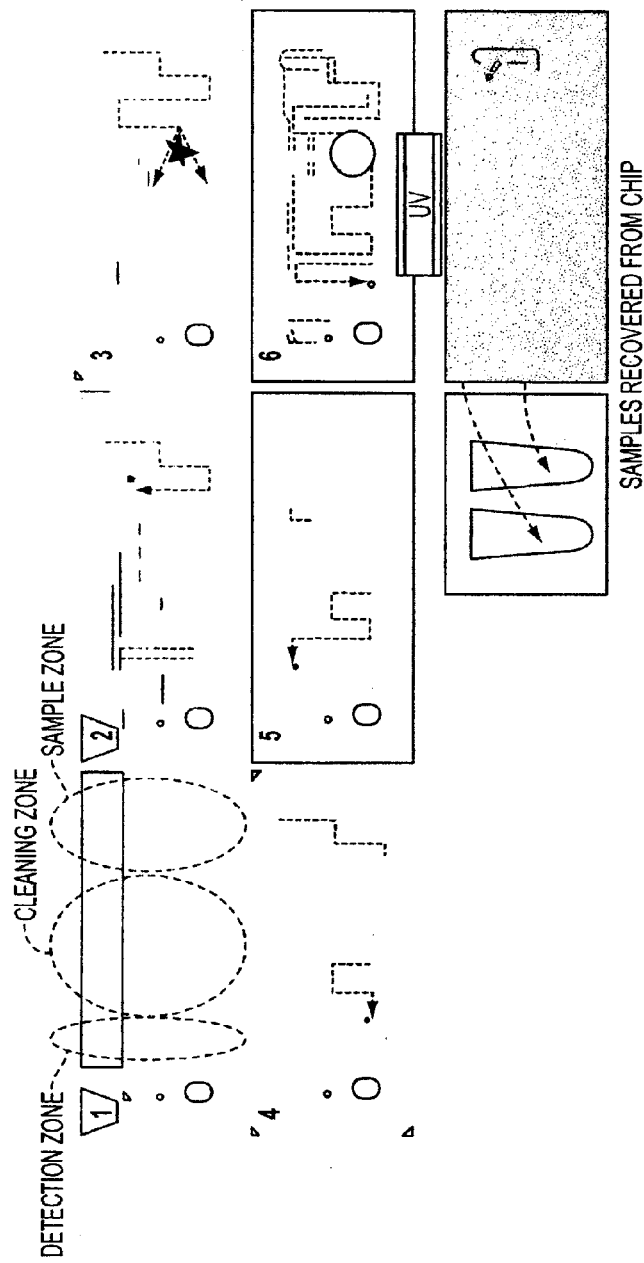

FLEX DISTRIBUTION CONTROL

CONTROLLED BY POLARITY OF CURRENT

CONTROLLED BY GEOMETRY OF CORE HEADS

CIRCUIT DESIGN FOR REVERSIBLE MAGNETIC FIELD

CIRCUIT DESIGN TO REDUCE # OF SWITCHES

| DIMENSIONS: | 36 GAUGE COPPER WIRE<br>350 TURNS (N), ID = 1.15 mm |
|---|---|
| INDUCTANCE: | $L = \mu N^2 A/d = 77$ mH |
| RESISTANCE: | $R = 5-8 \Omega$ |
| FIELD STRENGTH:<br>(CENTER, VERTICAL 300mA) | THEORETICAL: $\mu_{Fe} \mu_0 I n = 211$ GAUSS MEASURED:<br>340 GAUSS |
| TRANSIENT TIME: | $\tau = L/R = 10\text{-}15$ ms, TRANSITION AT $5\tau = 60\text{-}75$ ms |
| ENERGY IN MAGNETIC FIELD: (300mA) | $E = 0.5 L I^2 = 3.5$ mJ (NEEDS TO DISSIPATE) |

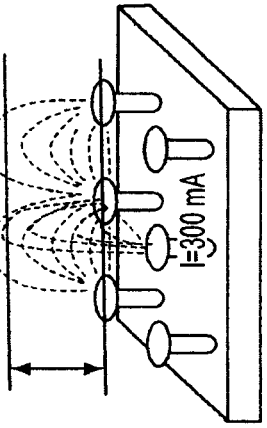

MAGNETIC FIELD AT 300mA

| HEIGHT (h) | - | COVER GLASS 0.2 mm | BIOCHIP 0.5 mm | GLASS SLIDE 1.2 mm |
|---|---|---|---|---|
| | 0 mm | | | |
| VERTICAL FIELD STRENGTH | 340 G | 293 G | 230 G | 166 G |

FIG. 14

DEVICE AND METHOD FOR PARTICLE COMPLEX HANDLING

CROSS-REFERENCE RELATED APPLICATIONS

This application is a continuation application of U.S. application Ser. No. 13/430,171, filed Mar. 26, 2012, now patented as U.S. Pat. No. 8,795,523 issued on Aug. 5, 2014, which is a divisional application of U.S. application Ser. No. 13/197,918, filed Aug. 4, 2011, now patented as U.S. Pat. No. 8,158,008 issued on Apr. 17, 2012, which is a divisional application of U.S. application Ser. No. 11/647,566, filed Dec. 29, 2006, now patented as U.S. Pat. No. 7,993,525 issued on Aug. 9, 2011. The disclosure of the prior applications is considered part of and is incorporated by reference in the disclosure of this application.

FIELD OF INVENTION

The embodiments of the invention relate to devices for conducting biomedical assays, methods of making such devices, and methods of detecting the presence of an analyte using such devices. More specifically, the embodiments relate to devices and methods that combine fluidic or fluid handling devices and magnetic microarrays with an integrated circuitry element that perform versatile and/or convenient analysis of an analyte with design flexibility. The invention transcends several scientific disciplines such as biochemistry and physics, engineering, microelectronics, microelectromechanical systems (MEMS), analytical chemistry, and biomedical diagnostics.

BACKGROUND

Chemical analysis and biomedical diagnostics commonly use absorption, fluorescence, chemiluminescence, UV-Vis and Raman scattering to detect the presence of an analyte. For example, enzyme-linked immunosorbant assays (ELISA) are widely used to detect an analyte. ELISA assays are typically performed in microwell plates, and require multiple steps of adding reagents, washing the reactant plates, and applying a reaction substrate that is converted to provide a chromogenic (colorimetric) or fluorescent signal. Furthermore, its detection limit ranges from the micromolar to picomolar or nanograms to pictograms of protein analyte per milliliter of a sample. For markers with low copy numbers, more sensitive detection technology is needed.

The current methods and devices for detecting the presence of an analyte in a sample have multiple drawbacks. First, the sizes of the devices are too big to be used in field applications or at home environment, such as point-of-care (POC) environment. Second, the current devices require a large amount of sample, which not only is infeasible for certain applications, but also hinders activities such as mixing and heating of the sample required for many analyses. Third, the current devices have complex structures for fluidic control and are often not self-contained. Fourth, current devices are limited by their detection sensitivity. Fifth, the current devices are often designed for specialized applications, e.g. protein analysis only, or nucleic acid only. Thus, there is a need for miniaturized, integrated, and versatile devices for analysis of a sample suspected of containing an analyte that can perform on-site, flexible, rapid, sensitive, and/or efficient analysis.

BRIEF DESCRIPTION OF THE DRAWINGS

FIG. 6A illustrates the use of the fluidic network in moving magnetic particles. FIG. 6B illustrates the fluorescence of a mixture of magnetic particles and Qdots, before and after washing.

FIG. 14 illustrates the data and specification of a prototype system, indicating magnetic coil structure and magnetic field strengths relatively to coil head surface.

DETAILED DESCRIPTION

Figure 1:
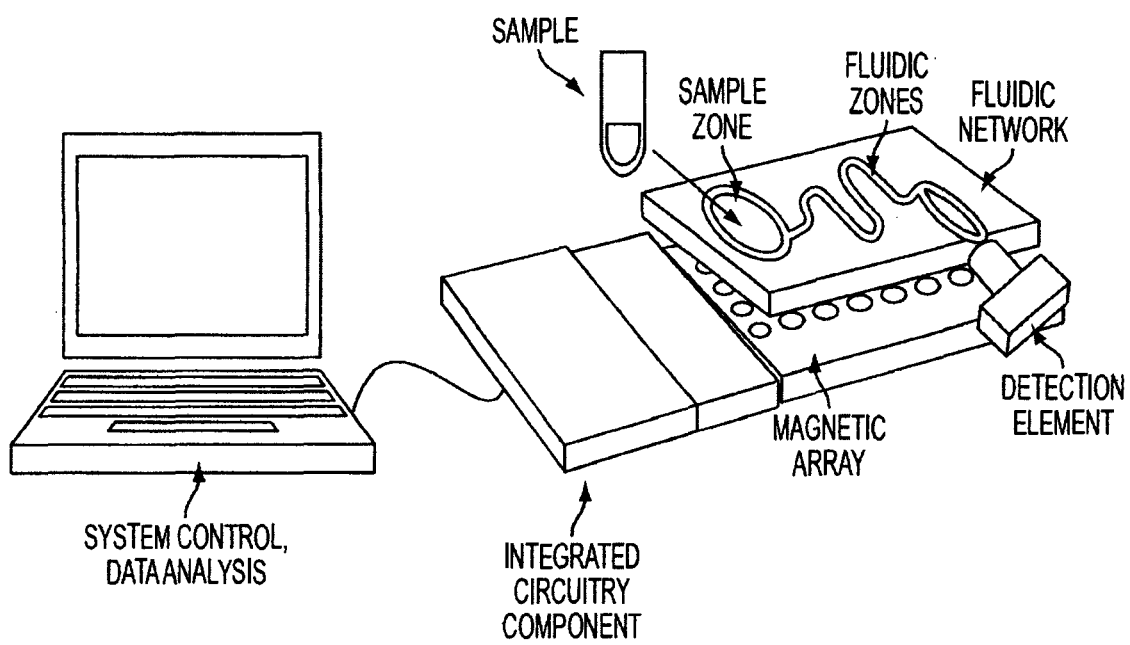
FIG. 1 illustrates an embodiment of the invention that comprises a fluidic network having a sample zone and other fluidic zones, associated with a magnetic microcoil array, a detection element and an integrated circuitry component, linked to a circuit board.

The embodiments of the invention relate to a device for detecting the presence of an analyte in a sample. The device comprises a fluidic network and an integrated circuitry component, functionally coupled to a magnetic microcoil array, a detection element, a circuit board, and optionally, a vibration element. Specifically, the fluidic network comprises a plurality of fluidic zones, where each zone is connected to the adjacent zone by a diffusion barrier. Typically one or more of the fluidic zones contains a magnetic particle and/or a signal particle. A sample suspected of containing an analyte is introduced into a fluidic zone. The analyte interacts with a magnetic particle and/or a signal particle to form a binding complex. The magnetic microcoil array is activated to generate a magnetic field across at least a portion of a fluidic zone to separate magnetic particles and binding complexes from uncomplexed signal particles and to move the binding complexes to a fluidic zone where it can be detected by the detection element. The device may further comprise servo-mechanical components and mechanisms to control the locations and movements of the detection element, the magnetic microcoil array, and optionally, a flow controller.

The embodiments of the invention also relate to methods of detecting the presence of an analyte in a sample using the device and to methods of making the device. The detection element of the embodiments of the invention may be part of an integrated device that also serves as a microarray or macroarray, containing an integrated circuitry component, or a microfluidic device, a MEMS, or a combination thereof. Therefore, samples contained or processed by the device may be also analyzed by the detection element and/or the detection signals processed for analysis. If necessary, the signals determined by the detection element may be transmitted to another device for further analysis.

The embodiments of the invention relate to a device and method to transport particle complexes from one solution zone to another of a self-contained fluidic device without active liquid movement. It also allows for effective reactions along the fluidic channel network involving concentrating, dispersing and transporting particles of micro or nano dimensions. The device comprises the following major components: a) electromagnetic array, b) a set of vibrational elements, and c) a circuitry for electronic control and regulation of the magnetic array, the vibrational elements and data collection elements.

The embodiments of the invention address the problem of molecular or particulate transport in one fluidic zone to another in a fluidic system without active fluidic movement or using fluid as the transport carrier. Presently the problem described above is solved by method in which molecules are physically separated from one solution phase before being placed in another solution phase; or the molecules are immobilized on solid surfaces and a new solution is introduced involving active fluidic movement. The technical advantage of the embodiments of the invention is that it allows molecular or particulate transport in one fluidic zone to another in a fluidic system without active fluidic movement or using fluid as the molecular transport carrier, which avoids mechanical structures to generate hydraulic pressure or flow, enabling simple and reliable biomedical diagnostic devices. The mixing of reagents from one region with those of another due to diffusion can be reduced by geometric considerations to the level where no mechanical valves are needed to avoid unwanted diffusional mixing, or the hydrophilic reagent solution "droplets" are physically suspended in hydrophobic liquid such as silicone oils through hydrophobic-hydrophilic interactions.

The embodiments of the invention relate to a device for particle complex transport and detection comprising (1) an array of electromagnetic coils wherein the coil has a magnetizable or high magnetic permeability metal core, and the current for the coil can be controlled and varied in time individually, as well as reversed, to generate a specific magnetic flux distribution and gradient; there can be a magnetizable or high magnetic permeability coupling shape at the end of each coil whose geometry is such to create an optimal magnetic flux, intensity and gradient, in the region of interest; and the device is functionally coupled to a fluidic device to concentrate, disperse and transport particle complexes; (2) A detection system, of optical or electrical nature; for optical: an optical detection system consisting of a lens system and photo-diode, phototube or CCD sensing element, optionally, an optical illumination system consisting of a photo-diode, LED (light emitting diodes), laser or lamp, and a spectroscopy system which could contain diachronic mirror or lens; for electrical detection, the methods can be FET detection, capacitor detection, current and voltage detection; and (3) a central processing unit (CPU) functionally coupled to the array and data/signal collection elements (optical or electrical). The device of the embodiments of the invention could optionally have the following elements: (1) A set of magnetizable material shapes which are free to be moved by the magnetic field generated by the electromagnets and thereby alter the magnetic field. For example, a set of magnetic high mu metal or permanent magnetic objects that can be moved by powering electromagnets. The movement and placement of these objects will change the field enhancing and depleting it where needed. These magnetic shapes can be part of the array (coil cores), around the array (between array and fluidic device) or part of the fluidic device. (2) A set of vibrational elements, functionally coupled to a fluidic device to disperse particle complexes, preferably, being electro-piezo vibration, or ultrasounds, wherein one or more vibrational elements could be addressable individually. (3) A set of temperature controlling elements. For example, a set of element that can change the temperature of the fluidic device. Heating by inductively driving current in coils the fluidic device using the inductor array or electronic peltier devices. (4) A programmable system that can control the electromagnetic array in a set time sequence as well as vary the sequence depending on input from sensing elements. Controlling the vibrational or mixing elements, the temperature controlling elements and optical elements. Monitoring particle complexes within the fluidic device magnetically and optically. (5) A system to move the alignment of the fluidic device relative to the magnetic array and optical and vibrational or mixing elements.

As used in the specification and claims, the singular forms "a", "an" and "the" include plural references unless the context clearly dictates otherwise. For example, the term "an array" may include a plurality of arrays unless the context clearly dictates otherwise.

As used herein, "magnetic particle" refers to a paramagnetic or superparamagnetic particle having any shape, e.g. it can have the form of a sphere, a cylinder, a cube, an oval etc., or may have a variable shape. Different types of magnetic particles which can be used with the present invention are described, for example, by Urs Hafeli et al. in "Scientific and Clinical Applications of Magnetic Carriers", Plenum Press, New York, 1597, ISBN 0-306-45687-7. In one embodiment the magnetic particle comprises a streptavidin-coated magnetic bead. The magnetic particles can be quite small, having at least one dimension ranging between 0.1 nm and 10,000 nm, preferably between 3 nm and 500 nm, and more preferably between 10 nm and 300 nm. The magnetic particles can acquire a magnetic moment due to an applied magnetic field (e.g., they can be paramagnetic) or they can have a permanent magnetic moment. The magnetic particles can be a composite, e.g., consist of one or more small magnetic particles inside or attached to a non-magnetic material, or a hetero/hybrid nanostructures, such as dumbbell-shaped magnetic gold nanoparticles, which are composed by one half of magnetic particle and another half of gold nanoparticle. As such, the term "magnetic particle" encompasses magnetic affinity complexes, coded magnetic affinity complexes, hybrid magnetic complexes, and coded magnetic signal affinity complexes, among others. In certain embodiments, the sample zone of the fluidic device comprises the magnetic particle. In other embodiments, different or the same magnetic particles can be contained within more than one fluidic zone.

As used herein, a "magnetic affinity complex" comprises a magnetic particle functionally coupled to an affinity agent. The term "affinity agent" generally refers to a molecule that binds to an analyte for the detection and/or analysis of the analyte and is described in more detail below. Non-limiting examples of affinity agents include example of affinity agents including antibodies, lectins, streptavidin, oligonucleotides, peptides, and oligosaccharides. It can be coupled to the magnetic particle using a functionalized polymer, for example.

A "coded magnetic affinity complex" comprises a magnetic particle functionally coupled to an affinity agent and to a code. A "code" is a recognizable structure/molecule such as a polynucleotide sequence that correlates to the affinity agent and thus can be used to identify or quantify the analyte.

A "coded magnetic signal affinity complex" comprises a magnetic signal particle functionally coupled to an affinity agent and to a code. A "magnetic signal particle" is a nanoparticle having magnetic properties that is detectable by the detection element of the fluidic device. It can be detected by various means, including electrical sensing methods (i.e., FET), optical methods (UV-Vis, IR, Raman, fluorescence, chemiluminescence, evanescence, surface plasmon), magnetic imaging methods (such as MRI), enzymatic methods (production of a reaction product due to the interaction of a catalytic element with a reaction substrate, or alternatively, the amplification of a polynucleotide by PCR), and non-enzymatic chemical amplification methods.

A "signal particle" is a nanoparticle that is detectable by the detection element of the device, and thus encompasses signal affinity complexes, signal analyte complexes, and coded magnetic signal affinity complexes, among others. In certain embodiments the signal particle is a surface-enhanced Raman spectroscopy (SERS)-active nanoparticle, a fluorescent nanoparticle, a nanoparticle coupled to a surface-enhanced fluorescent tag, a nanoparticle containing contrast reagents, or a core nanoparticle covalently coupled to a catalytic element. In one embodiment, the signal particle is a COIN (composite organic-inorganic nanoparticles) particle. In other embodiments, the signal particle is a Qdot (quantum dot), or another fluorescent nanoparticle, such as SEF (surface-enhanced fluorescence) nanoparticle or a FluoDot™. In further embodiments, the signal particle is any nanoparticle (i.e. gold, silver, CdS, CdSe, copper, $Eu^{3+}$-coated polymer, an organic polymer (homo or hetero), polymer particles incorporated with organic dyes, an inorganic compound, or composite compounds, etc.). Additionally, the SERS-active nanoparticle and fluorescent nanoparticle can also be functionally coupled to a catalytic element. In certain embodiments, the sample zone of the fluidic device comprises the signal particle. Alternatively, the sample particle is contained within another fluidic zone. In further embodiments, different or the same signal particles can be contained within more than one fluidic zone.

A "signal affinity complex" comprises a signal particle functionally coupled to an affinity agent. A "signal analyte complex" refers to a signal particle functionally coupled to an analyte. An "analyte" refers to a molecule or biological cell of interest that is to be analyzed or detected using the devices and methods described herein, and is described further below.

A "catalytic element" is a compound that serves as an agent to cause a chemical reaction to occur in a reaction substrate, where the reaction product is detectable by the detection element. In certain embodiments, the catalytic element is selected from the group consisting of alkaline phosphatase, horseradish peroxidase, glucose oxidase, firefly luciferase, *Renilla* luciferase, bacterial luciferase, other enzymes or analogs or combinations thereof.

The catalytic element can be conjugated to the signal particle through a functionalized polymer. For example, a polymer with a functional group (i.e. aldehyde, amine, carboxylic acid, biotin) is used to conjugate the affinity agent and/or catalytic element to the signal particle. Conjugation or bio-conjugation can be through non-covalent interactions such as hydrophobic or electrostatic interactions, or through covalent interactions, such as amide bond formation.

The analyte interacts with the magnetic particle and/or signal particle to form a binding complex, which includes any combination of the above-described magnetic particles and signal particles. Binding complexes include for example, sandwich binding complexes, magnetic binding complexes, signal binding complexes, competitive binding complexes, coded magnetic binding complexes, and coded magnetic signal binding complexes.

A "sandwich binding complex" comprises a magnetic affinity complex, a signal affinity complex, and an analyte. For example, a sample suspected of comprising an analyte is introduced into the sample zone of the fluidic device. The analyte interacts sequentially or simultaneously with a magnetic affinity complex and a signal affinity complex to form a sandwich binding complex. Typically the affinity agent coupled to the magnetic particle is different than the affinity agent coupled to the signal particle, although both are complementary to the analyte. The microcoil array is activated to move the sandwich binding complex to the detection zone. Uncomplexed signal particles are left behind without being transported. The signal detected from the sandwich binding complex indicates the presence of the analyte. Typically this method is useful for determining the presence of proteins (including peptides, antibodies and autoantibodies) or nucleic acids.

A "super-binding complex" comprises a magnetic affinity complex, analyte, a coded affinity complex, and a-signal affinity complex. For example, a sample suspected of comprising an analyte is introduced into a fluidic zone and combined with a magnetic affinity complex to form a magnetic binding complex. The array of microcoils is activated to move the magnetic binding complex to a zone of the fluidic network comprising a coded affinity complex, which in one embodiment, is not magnetic. The magnetic binding complex and the coded affinity complex form a coded sandwich binding complex. The array of microcoils is activated to move the coded sandwich binding complex to a zone of the fluidic network comprising a signal affinity complex, wherein the coded sandwich binding complex and signal affinity complex form a super-binding complex. This transport moves the coded sandwich binding complex away from the unbound coded affinity complex. The microcoils are again activated to move the super-binding complex away from unbound signal affinity complex and to the detection zone, where it is detected, and where detection of the super-binding complex indicates the presence of the analyte.

A "coded affinity complex" comprises a particle functionally coupled to an affinity agent and a code. It is contemplated that the particle in such a complex may or may not be magnetic.

A "magnetic binding complex" comprises a magnetic affinity complex and an analyte.

A "signal binding complex" comprises a signal affinity complex and an analyte.

A "competitive binding complex" comprises a magnetic affinity complex and a signal analyte complex. A competitive binding complex can be formed using the methods and devices of certain embodiments of the invention. For example, a sample suspected of comprising an analyte is introduced into the sample zone of the fluidic device, wherein a magnetic affinity complex binds to the analyte to form a magnetic binding complex. The microcoil array is activated to move the magnetic binding complex from the sample zone to another fluidic zone. The analyte is displaced from the magnetic binding complex with a signal analyte complex. The combination of the signal analyte complex and the magnetic binding complex forms a competitive binding complex. The signal detected from the signal analyte complex that did not form the competitive binding complex indicates the presence of the analyte. Typically this method is useful for determining the presence of a small molecule, such as, but not limited to, sugars, drugs, steroids, and vitamins. In an alternative binding scheme: a) competitive binding complexes are pre-formed with magnetic affinity complex and analyte-conjugated signal affinity complex, b) the competitive binding complexes are directed to sample zone, where sample analyte displaces analyte-conjugated signal affinity complexes, c) the magnetic binding complexes are moved away from the sample zone by activating the microcoil array, and d) displaced analyte-conjugated signal affinity complex are detected in the sample zone, wherein the signal strength is proportional to the amount of sample analyte.

A "coded magnetic binding complex" comprises a magnetic affinity complex, an analyte, and a code. A "coded magnetic signal binding complex" comprises a magnetic signal affinity complex, an analyte and a code. Both of these binding complexes can be formed using the methods and devices of certain embodiments of the invention. Typically, a sample suspected of comprising an analyte is introduced into the sample zone of the fluidic device, wherein a coded magnetic affinity complex binds to the analyte to form a coded magnetic binding complex. The microcoil array is activated to move the coded magnetic binding complex from the sample zone to a first affinity surface, where it is bound and immobilized. Typically the affinity agent on the first affinity surface is complementary to and binds to the affinity agent on the magnetic particle. The code is then detached from the coded magnetic binding complex. The detached code then binds to a magnetic signal affinity complex to form a coded magnetic signal binding complex. Typically the affinity agent of the magnetic signal affinity complex is complementary to the code. In one embodiment, the affinity agent of the magnetic signal affinity complex is a polynucleotide complementary to the code polynucleotide. The microcoil array is activated to move the coded magnetic signal binding complex to one or multiple detection zones comprising a second affinity surface. Typically different areas of the detection zone or the different detection zones contain unique affinity agents to the codes. The affinity agents of the second affinity surface are complementary to and bind the code. The detection element then detects the coded magnetic signal binding complex in the detection zone using electrical sensing methods, optical sensing methods, or enzymatic methods, such as amplifying the affinity agent (if it is a polynucleotide) on the magnetic signal affinity complex.

It is contemplated that the analyte will bind to the affinity agent coupled to the magnetic particle, the signal particle, and/or the affinity surface. "Binds to" refers to the interaction of the analyte with the affinity agent, which is typically a non-covalent interaction. The interaction of the analyte with the affinity agent can be characterized in terms of a binding affinity. Binding affinity can be readily determined using standard technology. For example, the BIAcore™ system (Uppsala, Sweden) is one method for determining binding affinity. The BIAcore™ system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore™ analysis conveniently generates association rate constants, dissociation rate constants, equilibrium dissociation constants, and affinity constants. In certain embodiments, the affinity agent binds to the analyte with a binding affinity of at least $10^3$ $M^{-1}$, more preferably at least $10^5$ $M^{-1}$, and still more preferably, at least $10^7$ $M^{-1}$.

A "substrate" refers to a material or a combination of materials upon and/or within which other or additional materials are formed, attached, or otherwise associated with according to a predetermined fashion. A substrate often provides physical and functional support to the other or additional materials such that, together, they form part or whole of a functional device. A substrate may be a combination of two or more other substrates, which, due to the combination, have become an identifiable new substrate. In the embodiments of the invention, the substrate may comprise metal, silicon, glass, or polymeric materials. In more specific embodiments, the substrate contains an integrated circuitry component, and is functionally coupled to a magnetic microcoil array, a vibration element, a detection element, and/or a circuit board.

A "microcoil" is a coil, or one or more connected loops, having at least one dimension in the micrometer (μm), or less than $10^{-3}$ meter (mm), scale. A microcoil usually comprises a thin material wound or gathered around a center or an imaginative center into spiral, helical or other shapes. A microcoil is defined by the material itself, the shape of the windings, and the separation between each windings. Solenoid type microcoils are multiple spiral wire loops, which may or may not be wrapped around a metallic core. A Solenoid type microcoil produces a magnetic field when an electrical current is passed through it and can create controlled magnetic fields. A Solenoid type microcoil can produce a uniform magnetic field in a predetermined volume of space. A "planar" microcoil is a microcoil with its windings substantially remained in an actual or imaginative plane. Microcoils can also be fabricated into MEMS devices such as demonstrated by MEMS magnetic actuators (IEEE Journal of Solid-State Circuits (2006) 41:1471 and Biosensors and Bioelectronics (2006) 21:1693.

The embodiments of the invention contemplate the activation of one or more microcoils (or to the movement of a permanent magnet) in order to move the magnetic particles and/or binding complexes. "Activation" or "activating" refers to turning on one or more microcoils while turning off (or keeping off) one or more other microcoils, which causes the magnetic particles (and any component attached to the magnetic particle) to move towards the microcoil(s) in the on position and away from the microcoil(s) in the off position.

As used in the embodiments of the invention, "associated with" is used interchangeably with "functionally coupled" and means that two or more objects are so situated that the desired results or effects are achieved. For example, a microcoil array is "functionally coupled" with the fluidic device when one or more microcoils are so situated that they will achieve the desired effect of generating an magnetic field within at least a portion of a fluidic zone of the device. Such coupling can be permanent, where the microcoil array is integrated into the fluidic device, or temporary, where the microcoil array is adjacent or in proximity to the device but is not integrated into the device. Similarly a vibration element is also "functionally coupled" with the fluidic device when it is so situated that it will achieve the desired effect of shaking, mixing, or agitating fluid within one or more fluidic zones of the device. Again, the vibration element can be integrated into the device, or can be in proximity to the device. In certain embodiments, the vibrational element agitates the fluid in one or more fluidic zones to disperse the magnetic particles, analyte, and/or signal particles so that they can interact to form a binding complex. In other embodiments, the vibrational element agitates the fluid in one or more fluidic zones to facilitate aggregation-disaggregation and removal of unbound signal particles and/or non-analyte components of the sample from the binding complex. In another embodiment, the mixing is demonstrated on a MEMS devices (IEEE Proc. Int. Conf. MEMS'02 (2002), 40-43). The detection element is "functionally coupled" with the fluidic device when it will achieve the desired effect of detecting and/or measuring the presence of the analyte (or binding complex) within the detection zone of the device. The detection element can be integrated into the device, or can be in proximity to the device. The flow controller is "functionally coupled" with the fluidic device when it will achieve the desired effect of coordinating liquid flow through the fluidic zones of the device.

A number of factors will be considered when associating the microcoil array, the vibration element, the detection element, or the flow controller with the fluidic device, including the sizes and shapes of the substrate, the type and size of the microcoil array, the size and location of the fluidic zones, the number of the fluidic zones, the desired strengths of the magnetic field and, and the volume within which the binding complex or signal particle is to be detected. As disclosed herein, the specific locations of the magnetic microcoil array, the detection element and the vibration element with respect to the fluidic device will be determined based on the specific analysis desired by a person skilled in the art.

As used herein, "dimension" or "dimensions" are the parameters or measurements required to define the shape and/or size, such as height, width, and length, of an object. As used herein, the dimension of a two-dimensional object, such as a rectangle, a polygon, or a circle, is the longest straight-line distance between any two points on the object. Therefore the dimension of a circle is its diameter; a rectangle its diagonal, and a polygon its longest diagonal. The dimension of a three-dimensional object is the longest straight-line distance between any two points on the object. The dimensions used herein are usually measured by centimeters (cm), millimeters (mm), and micrometers (µm), and nanometers (nm).

A "fluidic device" or "fluidic network" is a device that has one or more fluidic zones that are capable of containing a liquid. A fluidic device may be functionally coupled to other components, such as a magnetic microcoil array, a vibrational element, a detection element, a circuit board and a circuitry component. Fluids used in the fluidic devices include bodily fluids such as, but not limited to, amniotic fluid, aqueous humor, bile, blood and blood plasma, breast milk, cerebrospinal fluid, cerumen, colostrum, chyle, chyme, feces, female ejaculate, interstitial fluid, intracellular fluid, lymph, menses, mucus, pre-ejaculatory fluid, pleural fluid, pus, saliva, sebum, semen, serum, sweat, synovial fluid, tears, urine, vaginal lubrication, vitreous humor, and vomit; bacterial cell suspensions; protein or antibody solutions; various buffers; saline; and reaction substrates. The sample introduced into the fluidic device typically comprises a liquid, gel, solid, gas, or mixture thereof, suspected of containing an analyte. Fluidic devices can be used to obtain many interesting measurements, including fluid mechanical properties, cellular and molecular diffusion coefficients, fluid viscosity, pH values, chemical and biological binding coefficients and enzyme reaction kinetics. Other applications for fluidic devices include cell and molecule detection and separation, capillary electrophoresis, isoelectric focusing, immunoassays, flow cytometry, sample injection of proteins for analysis via mass spectrometry, DNA analysis, cell manipulation, and cell separation. In one embodiment of the invention, magnetic materials and technologies and/or nanoparticles are incorporated into the fluidic devices for applications such as cell and biomolecule detection and/or separation. As used herein, the term "detecting the presence" refers to determining the existence, identity, and/or amount of an analyte in a particular sample.

A "fluidic zone" is typically a reservoir, channel, groove, opening, or conduit in the substrate of the fluidic device, which is configured for containing a liquid and optionally for containing reagents. Fluidic zones can be straight along their length, however, they can also contain angles and curves of different degrees along their length. The fluidic zones can have rectangular cross-sections, or they may also have other shapes of cross-sections, such as circular. Typically the fluidic zone has at least one dimension in the micrometer or millimeter scale.

The fluidic zones may be suitable for fluidic communications, such as carrying a biological liquid to an adjacent fluidic zone. Alternatively, the fluidic zones may be suitable for non-fluidic communications, such as carrying through molecules or compounds in the absence of significant active hydraulic fluid transport or exchange. Such molecules or compounds are typically magnetic particles, nanoparticles, affinity agents, analytes, and combinations thereof. The fluidic zones are often part of an integrated device, such a fluidic device, such that liquid, molecules or compounds flowing through the fluidic zones occurs in a controlled pattern and are able to be analyzed as desired.

The fluidic device typically comprises a plurality of fluidic zones. In one embodiment, the plurality of fluidic zones comprises a sample zone, a cleaning zone and/or a detection zone. In a further embodiment, it comprises more than one sample zone, cleaning zone, and/or detection zone. It can comprise additional fluidic zones for storing reagents, which can be branches of any of the aforementioned zones. In one embodiment, multiple fluidic zones are contained in parallel within the same device, thus allowing for analysis of multiple samples or multiple analytes in parallel. Each fluidic zone is separated from the adjacent fluidic zone by a diffusion barrier.

A "diffusion barrier" is a structure to minimize diffusion or convectance of the contents of one fluidic zone to the next fluidic zone, such that the majority of the contents that move from one zone to the next fluidic zone are moved by directed fluidic flow and/or by activating the magnetic microcoil array. Diffusion barriers can be created, for example, by elongating the channel, groove, opening or conduit ("the path of the fluidic zone"), narrowing the path, angling the path of the fluidic zone, or any combination thereof. Diffusion barriers can also comprise a physical barrier, such as thermally-sensitive barrier. A "thermally-sensitive barrier" is a physical barrier that becomes permeable due to the application of heat. For example, a thermally-sensitive barrier can comprise a gel that melts when heated and thus allows the contents of one fluidic zone to pass through to the next zone. Hydrophilic fluid or liquid can be contained in a shape of droplets surrounded by hydrophobic liquid such as silicone oils to form strong diffusion barriers through hydrophilic-hydrophobic interactions so that droplets can be separated and transported without mixing with other fluids as demonstrated in J. Micromech. Microeng. (2006) 16:1875 and Sensors and Actuators B (2006) 113:563. A diffusion barrier can be accomplished by "particle trapping and transport" through DEP (dielectrophoresis) as demonstrated in Biophysical Journal (1998) 74:1024 and Sensors and Actuators A 121 (2005) 59. In yet another aspect, the diffusion barrier can be created by a MEMS membrane valve.

The sample zone comprises a space for holding a sample, and is selected from a reservoir, a channel, an opening, a surface, or a combination thereof. In one embodiment, there is an inlet for allowing the insertion of a sample into the zone, and a vent to allow air or gas to exit as the sample is introduced. In a further embodiment, the vibration element is activated to vibrate the fluid within the sample zone and deaggregate the magnetic particles, signal particles, analyte, and/or binding complexes, in order to facilitate interaction between these components and allow for separation of unbound components from the binding complexes.

The cleaning zone is a reservoir, channel, groove, opening, or conduit connecting the sample zone and the detection zone, which is preferably separated from the sample zone and detection zone by diffusion barriers. In one embodiment, an additional reaction between an analyte and a magnetic particle and/or a signal particle can occur in this zone. In other embodiments, this zone provides a region whereby the magnetic particles and binding complexes are separated from unbound analyte or other components of the sample, and/or unbound signal particles. In a further embodiment, the cleaning zone can comprise an affinity surface that is typically complementary to the affinity agent attached to the magnetic and/or signal particle, such that the particles are essentially immobilized in this zone.

The detection zone is a reservoir, channel, groove, opening, or conduit in association with a detection element. It may comprise an array of capture molecules, as described in more detail below. The detection element can be an optical detection element or an electrical detection element. In certain embodiments, the optical detection element is selected from a Raman detector, a photon multiplier tube, a fluorescent reader, or an electrochemical sensor and the electrical detection element is selected from a FET element, a capacity detection element, a current sensor, and a charge sensor. Typically, the detection of the binding complex or the signal analyte complex indicates the presence of the analyte.

In further embodiments, the detection zone comprises a reaction substrate. A "reaction substrate" is a material or substance upon which an enzyme (such as the catalytic element) acts. The product of the reaction can be fluorogenic, chemiluminescent, or detectable by UV-visible light (such as by a color change). Non-limiting examples of reaction substrates include Lumigen APS-5, Lumigen TMA-6, Lumigen PS-atto, Lumigen PS-3, $H_2O_2$ with an oxidizable compound, Amplex Red, 3,5,3',5'-tetramethylbenzidine (TMB), glucose, $O_2$, ATP, $Mg^{2+}$, luciferin, inoluciferin, quinolinyl, coelentrazine, aldehyde, $FMNH_2$, and analogs and combinations thereof.

Typically, if the detection zone comprises a reaction substrate, the magnetic affinity complex and/or the signal affinity complex comprises a catalytic element. The "catalytic element" is an external compound that serves as an agent to cause a chemical reaction to occur in the reaction substrate, which reaction product is detectable by the detection element. In certain embodiments, the catalytic element is selected from the group consisting of alkaline phosphatase, horseradish peroxidase, glucose oxidase, luciferase (from firefly, *Renilla*, bacteria, or other sources) or analogs or combinations thereof.

The catalytic element can be conjugated to the signal particle through a functionalized polymer. For example, a polymer with a functional group (i.e. aldehyde, amine, carboxylic acid, biotin) is used to conjugate the affinity agent and/or catalytic element to the particle. Conjugation can be through non-covalent interactions such as hydrophobic or electrostatic interactions, or through covalent interactions, such as amide bond formation.

Additionally, the fluidic zones of the device can contain an appropriate buffer to permit the reaction to occur.

Examples of non-limiting catalytic element-reaction substrate combinations and the method for detecting the reaction product are shown in Table 1.

TABLE 1

| Examples | Catalytic element | Substrate | Signal | Detection |
|---|---|---|---|---|
| 1 | Alkaline phosphatase (AP) | Lumigen APS-5 and others | Light (450 nm). | Photo sensor |
| 2 | Horse-radish peroxidase (HRP) | Lumigen PS-atto, Lumigen TMA-6, Lumigen PS-3, etc | Light | Photo sensor |
| | | $H_2O_2$, oxidizable compound | Electron | Electrical sensor |
| | | Amplex Red (10-acetyl-3,7-dihydroxyphenoxazine) + $H_2O_2$ | Fluorescence from resorufin | excitation at 530-571 nm, emission at 590-600 nm |
| | | 3,5,3',5'-tetramethylbenzidine (or its analogues) + H2O2 | Absorption (450 nm) | UV-Vis |
| 3 | Glucose oxidase | Glucose, $O_2$ | Electron | Electrical sensor |
| | Glucose oxidase (GO) + Horseradish peroxiadase (HRP) | a) Glucose, $O_2$ for GO b) Amplex Red for HRP | Fluorescence from resorufin | excitation at 530-571 nm, emission at 590-600 nm |
| 4 | Luciferase (firefly) | ATP + MG2+ + O2 + luciferin (or its analogues: aminoluciferin, quinolinyl luciferin) | light (560 nm) | Photo sensor |
| | Luciferase (Renilla) | Coelentrazine + O2 | light (475 nm) | Photo sensor |
| | Luciferase (Bacterial) | Aldehyde + FMNH2 + O2 | light (490 nm) | Photo sensor |

In certain embodiments, a fluorescent tag is attached to the signal particle. Non-limiting examples of suitable fluorescent tags include HcRed, green fluorescent protein, modified or enhanced green fluorescent protein, yellow fluorescent protein, enhanced yellow fluorescent protein, cyan fluorescent protein, blue fluorescent protein, red fluorescent protein, soluble-modified red-shifted green fluorescent protein, soluble-modified blue fluorescent protein; blue variant of green fluorescent protein; soluble-modified blue fluorescent protein, or analogs or combinations thereof.

In other embodiments, the signal particle is itself detectable by the detection element in the absence of a catalytic element and reaction substrate. Typically, in such situation, the signal particle will comprise a SERS-active nanoparticle or a fluorescent nanoparticle, which can, for example, comprise a nanoparticle coupled to a surface-enhanced fluorescent tag. The SERS-active nanoparticle is detectable by Raman in the detection zone. The fluorescent nanoparticle can be, for example, a Qdot or other fluorescent nanoparticles, such as SEF nanoparticles or FluoDots, which are detectable by examining fluorescence in the detection zone.

Alternatively, detection of the analyte can occur by fluorescence quenching. In one embodiment, the signal particle comprises a nanoparticle coupled to an affinity agent and an ODN sequence. The detection zone contains a FRET pair of double stranded ODNs that contain donor or acceptor on one strand each, and where one of the single strands is complementary to the ODN sequence on the nanoparticle. Interaction between the ODN and the FRET pair results in a decrease in fluorescence, thus indicating the presence of the analyte.

In a further embodiment, the analyte is detected by Fluorescence Resonance Energy Transfer (FRET). FRET is an energy transfer mechanism between two fluorescent molecules. A fluorescent donor is excited at its specific fluorescence excitation wavelength. By a long-range dipole-dipole coupling mechanism, this excited state is then non-radiatively transferred to a second molecule, the acceptor, where it is then released as a photon. In one embodiment, a sandwich binding complex is formed between a magnetic particle, an analyte, and a nanoparticle coated with one partner of a FRET pair in one zone, the sandwich binding complex is moved to a second zone where another partner of the FRET pair is present, and FRET is detected.

In a further embodiment, fluorescence is detected through the use of complimentary segments of the fluorophore. For example, a sandwich binding complex is formed between a magnetic particle, an analyte, and a nanoparticle coated with half of a fluorescent protein (such as GFP or an analog) in one zone, the sandwich binding complex is moved to a second zone where the other half of the fluorescent protein is present, the fluorescent protein self-assembles, and fluorescence is detected.

Fluorogenic detection can also be employed. In one embodiment, a binding complex is formed between a magnetic particle, an analyte, and an antibody-enzyme fusion protein in one zone, and it is moved to a second zone containing a fluorogenic reaction substrate, where the enzyme reacts with the reaction substrate to produce a detectable reaction product.

Time-resolved fluorescence can similarly be used in the invention. In one embodiment, a sandwich binding complex is formed between a magnetic particle, an analyte, and a nanoparticle encoded with $Eu^{3+}$ or $Tb^{3+}$ or another lanthanide in one zone; the binding complex is moved to another zone and detected by time-resolved fluorescence.

Other types of fluorescence can also be used, such as fluorescence polarization, and fluorescence life time studies.

Additionally, binding complex formation can be detected by chemiluminescence. As described above, a sandwich binding complex can be formed between a magnetic particle, an analyte, and a nanoparticle coated with a catalytic element in one zone, with chemiluminescent detection in another fluidic zone. Alternatively, a binding complex can be formed between a magnetic particle, an analyte, and an antibody-catalytic element fusion protein in one zone, with chemiluminescent detection in another zone. In a further embodiment, a binding complex can be formed between a magnetic particle, an analyte, and a silver nanoparticle or nanorod coated with affinity agents (such as antibodies) for recognition of the analyte and chelating agents for its metal ions (such as $Eu^{3+}$) in one zone, moving the binding complex to another zone where metal ions such as $Eu^{3+}$ are present, and detecting the binding complex by chemiluminescence.

Binding complex formation is also detectable via UV-visible spectroscopy. For example, a binding complex can be formed between a magnetic particle, an analyte and an antibody-catalytic element (such as horseradish peroxidase) in one zone and the complex is moved to another zone where it reacts with one or more HRP substrates and is detected by UV-visible spectroscopy.

Reflectance can be used to detect binding complex formation. For example, a binding complex can be formed between a magnetic particle, an analyte and a silver nanoparticle or nanorod coated with affinity agent specific for the analyte in one zone, the binding complex is moved to another zone, where it is detected by reflectance.

Binding complex formation can also be detected electrically, such as by current measurement (where there is oxidation and reduction or free electron production), FET or potential measurement (where there is net or local charge changes), or by CHEM-FET, surface plasmon resonance, mass spectroscopy, interferometry, or radioactivity. These methods of detection are merely non-limiting examples of the many possible methods of detecting the presence of a binding complex or signal particle in the detection zone of the fluidic device of the invention.

The use of fluidic devices to conduct biomedical assays has many significant advantages. First, because the volume of fluids within the fluidic zones is very small, usually several nano-liters, the amount of reagents and analytes required for the assays is quite small. This is especially significant for expensive reagents. The fabrications techniques used to construct these fluidic devices, discussed in more details herein, are relatively inexpensive and are very amenable both to highly elaborated, multiplexed devices and also to mass production, such as in an integrated circuit die. In manners similar to that for microelectronics, fluidic technologies also enable the fabrication of highly integrated devices for performing different functions on the same substrate chip. Embodiments of the invention helps create integrated, portable clinical diagnostic devices for home and bedside use, thereby eliminating time consuming laboratory analysis procedures. Additionally, certain embodiments of the invention are self-contained such that liquid does not flow through the fluidic zones, thereby eliminating the need for flow controllers. A self-contained fluidic network can also comprise pre-stored reagents, meaning during a test, no addition reagents need to be added except for the sample, and water or buffer. In such embodiments, the magnetic particles and any molecules bound to the magnetic particles are moved through the liquid contained within the fluidic zones by activating the magnetic microcoils, and are not moved by the flow of the liquid. Typically in these embodiments, the fluid is present in the fluidic zones to act as a suspending agent. Other embodiments of the invention comprise a flow controller for coordinating liquid flow through the fluidic zones of the device. In such embodiments, the magnetic particles and any molecules bound to the magnetic particles are moved through the fluidic zones by activating the magnetic microcoils and/or also can be moved by activating the flow controller to move the liquid itself.

As used herein, "magnetic," "magnetic effect," and "magnetism" refer to the phenomena by which one material exert an attractive or repulsive force on another material. Although theoretically all materials are influenced to one degree or another by magnetic effect, those skilled in the art understand that magnetic effect or magnetism is only recognized for its detectability under the specific circumstance.

As used herein, a "permanent magnet" is a material that has a magnetic field without relying upon outside influences. Due to their unpaired electron spins, some metals are magnetic when found in their natural states, as ores. These include iron ore (magnetite or lodestone), cobalt, and nickel. A "paramagnetic material" refers to a material that attracts and repels like normal magnets when subject to a magnetic field. Paramagnetic materials include aluminum, barium, platinum, and magnesium. A "ferromagnetic material" is a material that can exhibit a spontaneous magnetization. Ferromagnetism is one of the strongest forms of magnetism and is the basis for all permanent magnets. Ferromagnetic materials include iron, nickel, and cobalt. A "superparamagnetic material" is a magnetic material that exhibits a behavior similar to that of a paramagnetic material at temperatures below the Curie or the Neel temperature.

An "electromagnet" is a type of magnet in which the magnetic field is produced by a flow of electric current. The magnetic field disappears when the current ceases. A simple type of electromagnet is a coiled piece of wire that is electrically connected. An advantage of an electromagnet is that the magnetic field can be rapidly manipulated over a wide range by controlling the electric current. In the embodiments of the invention, ferromagnetic or non-magnetic materials are used to form the electromagnets.

An "array," "macroarray" or "microarray" is an intentionally created collection of substances, such as molecules, openings, microcoils, detectors and/or sensors, attached to or fabricated on a substrate or solid surface, such as glass, plastic, silicon chip or other material forming an array. The arrays can be used to measure the expression levels of large numbers, e.g., tens, thousands or millions, of reactions or combinations simultaneously. An array may also contain a small number of substances, e.g., one, a few or a dozen. The substances in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

An array of magnetic microcoils is a collection of microcoils fabricated on a substrate, such as silicon, glass, or polymeric substrate. Each of the microcoils may be associated with or functionally coupled to the fluidic device containing fluidic zones, across which the microcoil is capable of generating a magnetic field as part of a biomedical assay. The fluidic zones may be a space for holding a liquid sample and/or a surface for immobilizing certain molecules, such as DNAs and proteins. The microcoil arrays may be a microarray or a macroarray depending on the sizes or the microcoils and the associated sample spaces. In one embodiment, the microcoil array is programmably activatable such that individual members or groups of the array turn on and off in a coordinated manner in order to move the magnetic particles (and any compounds or molecules attached to the magnetic particles) from one fluidic zone to another fluidic zone. As used herein, "move" refers to changing the position of the magnetic particle, and includes concentrating and dispersing the particles as well as re-locating the particles within a fluidic zone and/or from one fluidic zone to another fluidic zone.

A DNA microarray is a collection of microscopic DNA spots attached to a solid surface forming an array. DNA microarrays can be used to measure the expression levels of large numbers of genes simultaneously. In a DNA microarray, the affixed DNA segments are known as probes, thousands of which can be used in a single DNA microarray. Measuring gene expression using microarrays is relevant to many areas of biology and medicine, such as studying treatments, disease and developmental stages.

"Solid support" and "support" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "molecule" generally refers to a macromolecule or polymer as described herein. However, channels or arrays comprising single molecules, as opposed to macromolecules or polymers, are also within the scope of the embodiments of the invention.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

The term "biomolecule" refers to any organic molecule that is part of or from a living organism. Biomolecules include a nucleotide, a polynucleotide, an oligonucleotide, a peptide, a protein, a ligand, an antibody, a receptor, among others. A "complex of a biomolecule" refers to a structure made up of two or more types of biomolecules. Examples of a complex of biomolecule include a cell or viral particles.

As used herein, "biological cells" and "cells" are interchangeable, unless otherwise clearly indicated, and refer to the structural and functional units of all living organisms, sometimes called the "building blocks of life." Cells, as used herein include bacteria, fungi, and animal mammalian cells. Specifically included are animal blood cells, such as red blood cells, white blood cells, and platelets.

The term "analyte" or "analyte molecule" refers to a molecule or biological cell of interest that is to be analyzed or detected, e.g., a nucleotide, an oligonucleotide, a polynucleotide, a peptide, a protein, an antibody, or a blood cell. Examples of analytes that can be investigated by this invention include, but are not restricted to, agonists and antagonists for cell membrane receptors, toxins and venoms, viral epitopes, hormones, hormone receptors, peptides, enzymes, enzyme reaction substrates, cofactors, drugs (e.g. opiates, steroids, etc.), lectins, sugars, polynucleotides, nucleic acids, oligosaccharides, proteins, antibodies, and autoantibodies. The analyte or analyte molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires and nanoparticles. The analyte in an assay can be a moiety or derivative generated by assay process, which is the subsequently recognized and detected as surrogate marker of the analyte contained in the sample. The analyte may be magnetically tagged, or labeled to facilitate its detection and separation.

The term "affinity agent" refers to a molecule that binds to an analyte for the detection and/or analysis of the analyte. The affinity agent generally, but not necessarily, has a known molecular structure or sequence. In one embodiment, the affinity agent is attached to a solid surface of the fluidic device. When the affinity agent is attached to a solid surface, it is referred to as an "affinity surface". In another embodiment, the affinity agent is attached to a magnetic particle or signal particle. When the affinity agent is attached to the magnetic particle, it is referred to as a "magnetic affinity complex". When the affinity agent is attached to the signal particle, it is referred to as a "signal affinity complex". In one embodiment of the signal affinity complex, the affinity agent is the analyte of interest; in such case, the signal affinity complex is termed a "signal analyte complex". The affinity agent typically include, but are not limited to antibodies, autoantibodies, cell membrane receptors, monoclonal or polyclonal antibodies and antisera reactive with specific antigenic determinants (such as on viruses, cells or other materials), drugs, polynucleotides, nucleic acids, peptides, proteins, cofactors, lectins, sugars, polysaccharides, cells, cellular membranes, and organelles. Affinity agents are biomolecules capable of undergoing binding or molecular recognition events with analytes. An affinity agent can be a capture molecule.

The term "capture molecule" refers to a molecule that is immobilized on a surface. The capture molecule can bind to the analyte, the magnetic particle, the signal particle, the affinity agent, or the code. The capture molecule is typically a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to an analyte that is bound to an affinity agent to form a complex of the capture molecule, analyte and the magnetic affinity complex and/or the signal affinity complex. The capture molecule may be magnetically or fluorescently labeled DNA or RNA. In specific embodiments of the invention, the capture molecule may be immobilized on the surface of a fluidic zone of the fluidic device. The capture molecule may or may not be capable of binding to just the analyte, or just the affinity agent.

The terms "die," "polymer array chip," "DNA array," "array chip," "DNA array chip," or "bio-chip" are used interchangeably and refer to a collection of a large number of probes arranged on a shared substrate which could be a portion of a silicon wafer, a nylon strip or a glass slide.

Certain embodiments of the invention contemplate the use of coded magnetic particles and signal particles for detecting the presence of an analyte using the devices described herein. Typically, a sample suspected of comprising an analyte is introduced into the sample zone of the fluidic device, wherein a coded magnetic affinity complex binds to the analyte to form a coded magnetic binding complex. The microcoil array is activated to move the coded magnetic binding complex from the sample zone to a first affinity surface, where it is bound and immobilized. Typically the affinity agent on the first affinity surface is complementary to and binds to the affinity agent on the magnetic particle. The code is then detached from the coded magnetic binding complex. The detached code then binds to a magnetic signal affinity complex to form a coded magnetic signal binding complex. Typically the affinity agent of the magnetic signal affinity complex is complementary to the code. In one embodiment, the affinity agent of the magnetic signal affinity complex is a polynucleotide complementary to the code polynucleotide. The microcoil array is activated to move the coded magnetic signal binding complex to one or multiple detection zones comprising a second affinity surface. Typically different areas of the detection zone or the different detection zones contain unique affinity agents to the codes. The affinity agents of the second affinity surface are complementary to and bind the code. The detection element then detects the coded magnetic signal binding complex in the detection zone using electrical sensing methods, optical sensing methods, or enzymatic methods, such as amplifying the affinity agent (if it is a polynucleotide) on the magnetic signal affinity complex.

"Detach" refers to the separation of the code molecule from the affinity agent of the magnetic particle. It can be detached using any method known to those of skill in the art. In one embodiment, it is detached by heating. In other embodiments, it is enzymatically detached.

The term "nucleotide" includes deoxynucleotides, ribonucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA) or linked polynucleotide (LNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

When the biomolecule or macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., an affinity agent polynucleotide of the invention which may include substitutions, deletion, and/or additions) and a specific analyte polynucleotide wherein the probe preferentially hybridizes to the specific analyte polynucleotide and substantially does not hybridize to polynucleotides consisting of sequences which are not substantially complementary to the analyte polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of analyte polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

The term "chip" or "microchip" refers to a small device or substrate that comprises components for performing certain functions. A chip includes substrates made from silicon, glass, metal, polymer, or combinations and capable of functioning as a microarray, a macroarray, a fluidic device, and/or an integrated circuitry component. A chip may be a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components. In the embodiments of the invention, as discussed herein, fluidic zones, magnetic microcoil arrays, detection elements, and vibration elements can also be integrated into a microchip.

"Micro-Electro-Mechanical Systems (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost. In the embodiments of the invention, as discussed herein, MEMS devices can be further integrated with fluidic zones, diffusion barriers, magnetic microcoil arrays, detection elements, and/or vibration elements, such that, together, they perform separation and detection function for biomolecules.

An "integrated circuitry component" is a processor on an integrated circuit (IC) chip. The processor may be one or more processor on one or more IC chip. The chip is typically a silicon chip with thousands of electronic components that serves as a central processing unit (CPU) of a computer or a computing device. It is typically a readable and writable memory chip, with or without contact. In certain embodiments, it can store reagent information, operation instructions and programs, and test results and data.

A "nanomaterial" as used herein refers to a structure, a device or a system having a dimension at the atomic, molecular or macromolecular levels, in the length scale of approximately 1-1000 nanometer (nm) range. Preferably, a nanomaterial has properties and functions because of the size and can be manipulated and controlled on the atomic level.

The term "complementary" refers to the topological compatibility or matching together of interacting surfaces of an analyte and its corresponding affinity agent. Thus, the affinity agent and its analyte can be described as complementary, and furthermore, the contact surface characteristics are complementary to each other. With respect to polynucleotides, sequences are complementary when they are able to hybridize to each other to form a stabilized duplex.

One embodiment of the invention relates to a device for detecting the presence or amount of an analyte in a sample. The device comprises a fluidic network and an integrated circuitry component which is functionally coupled to a magnetic microcoil array, a detection element, a circuit board, and optionally, a vibration element. In the embodiment, the fluidic network comprises a plurality of fluidic zones, where each zone is connected to the adjacent zone by a diffusion barrier. One or more of the fluidic zones contains a magnetic particle and a signal particle. A sample suspected of containing an analyte is introduced into a fluidic zone. The analyte interacts with a magnetic particle and the signal particle to form a binding complex. The magnetic microcoil array is to generate a magnetic field across at least a portion of a fluidic zone to move the binding complex to a fluidic zone where it can be detected by the detection element.

In one embodiment, the fluidic device integrates fluidic zones and a microcoil for generating a magnetic field within a portion of a fluidic zone. The fluidic zones and the microcoil may be supported by or integrated into a substrate. In another embodiment, the microcoil is placed near the substrate. When activated, the microcoil generates a magnetic field within a portion of a fluidic zone.

In a specific embodiment of the invention, the detection element of the substrate comprises silicon, glass, a polymeric material, metal, or a combination thereof. More specifically, the detection element may either comprise or be connected to an integrated circuit, a MEMS device, a microarray, a macroarray, a fluidic device, or a combination thereof. In other words, the embodiment can be integrated into or connected to a wide range of materials used in a variety of existing devices.

Silicon is a suitable material for forming micro-channels coupled with microelectronics or other microelectromechanical systems (MEMS). It also has good stiffness, allowing the formation of fairly rigid microstructures, which can be useful for dimensional stability. In a specific embodiment of the invention, the fluidic device or substrate comprises an integrated circuitry element (IC), a packaged integrated circuit, and/or an integrated circuit die. For example, the substrate may be a packaged integrated circuit that comprises a microprocessor, a network processor, or other processing device. The substrate may be constructed using, for example, a Controlled Collapse Chip Connection (or "C4") assembly technique, wherein a plurality of leads, or bond pads are internally electrically connected by an array of connection elements (e.g., solder bumps, columns).

Specific materials useful as the substrate also include, but not limited to, polystyrene, polydimethylsiloxane (PDMS), glass, chemically functionalized glass, polymer-coated glass, nitrocellulose coated glass, uncoated glass, quartz, natural hydrogel, synthetic hydrogel, plastics, metals, and ceramics. The substrate may comprise any platform or device currently used for carrying out immunoassays, DNA or protein microarray analysis. Thus, the substrate may comprise a microarray or a macroarray, a multi-well plate, a fluidic device, or a combination thereof.

In another embodiment, the fluidic device comprises circuitry that is capable of amplifying or processing the optical or electrical signals detected by the detection element. Any suitable conventional circuits may be used and integrated into the substrate for amplifying and/or processing, including filtering, the optical or electrical signals detected and collected by the detection element. The integrated circuitry may be able to generate a read-out of the optical or electrical signal independently or can be connected to an external device for generating the read-out.

In another embodiment of the invention, the sample is a liquid, a gel, a solid, a gas, or a mixture thereof. Therefore, the embodiment of the invention can accommodate samples in different physical states. In a specific embodiment, the sample is a liquid or in a liquid or solution state. In another embodiment, the sample zone comprises a reservoir, a channel, an opening, a surface, or a combination thereof. The embodiment accommodates a variety of applications in which a sample suspected of containing an analyte is to be analyzed. For example, the sample zone may be a reservoir, an opening void, or a surface that can hold a liquid sample. In such cases, the sample zone may be an open reservoir or surface, or a substantially closed void with an opening for sample input. The design of the space depends not only on the specific analysis to be done, but also on how to best situate and design the sample holding space in relation to the associated microcoil, detection element, and vibration element, as discussed herein.

According another embodiment, the sample zone for holding a sample, such as a liquid sample, may also be the whole or part of a channel fabricated on the substrate. Depending on the specific requirement, the channel may be open (a trench) or closed. The channel typically comprises an inlet and an outlet, but may also comprise other openings for fluidic communication. In another embodiment, the channel comprises two or more inlets and at least one outlet such that different reactants may be introduced into the channel from different inlets and mixed at a mixing section within the channel for specific chemical reaction. Furthermore, the channel may comprise more than two inlets and more than one mixing section such that more than one reaction may occur within different sections of the channel according predetermined manners. As discussed herein, the channel is designed in consideration with its relations with the associated microcoil, detection element, and vibration element to achieve the desired optical or electrical signal to detect the presence of the analyte.

In the embodiments of the invention, the sample zone of the device can accommodate a wide range of sample volume, including very small amount of samples. In one embodiment, the sample zone has a volume of from about 1.0 nL to about 1.0 mL. In another embodiment, the sample zone has a volume of from about 10 nL to about 10 µL. As understood by a person skilled in the art, actual sample volumes will depend on the nature of the analysis to be conducted, in addition to the design and dimensions of the device. In cases where the sample zone is a channel having two inlets and one outlet, the total sample zone may be substantially larger than the volume that is in proximity to a particular microcoil. For example, the total channel volume, excluding the inlets and outlet, may be about 1.0 µm while the volume in proximity to the microcoil may be about only 10 nL to 100 nL.

In the embodiments of the invention, many conductive materials are suitable for the microcoils. In the embodiments, the microcoil can be used for generating an excitation magnetic field across at least a portion of a fluidic zone. The selection of materials for the microcoil depends on several factors including the type and size of the coil, the desired strength of the magnetic field, the size and location of each fluidic zone, the shape, size and nature of the substrate, and the locations of the vibration element and detection element. The conductivity of the material is important to the selection. In one embodiment of the invention, the microcoil comprises copper, aluminum, gold, silver, or a mixture thereof.

In the embodiments of the invention, the microcoil is "functionally coupled" with the fluidic zones. A number of factors will be considered when functionally coupling the microcoil with the space, including the type and size of the microcoil, the sizes and locations of each fluidic zone, the desired strength of the magnetic field, and the volume within which the magnetic field will be effectuated. In a specific embodiment, the microcoil is placed near or adjacent to the fluidic zone. The specific type, size, strength, and location of the microcoil on the substrate will be determined based on the specific analysis desired by a person skilled in the art.

In one embodiment of the invention, the microcoil is a Solenoid type coil. Solenoid type microcoils are multiple spiral wire loops, which may or may not be wrapped around a metallic core. A Solenoid type microcoil, in addition to serving as a detection circuit, produces a magnetic field when an electrical current is passed through it and can create controlled magnetic fields. In the embodiment of the invention, the Solenoid type microcoil can produce a uniform magnetic field in a predetermined volume of the fluidic zone.

According to another embodiment of the invention, existing technologies can be used to construct the devices of the invention. For example, silicon process technologies can be used to construct or fabricate the fluidic device of the embodiments of the invention, such that the fluidic zones, diffusion barriers, and optionally the microcoils and vibration element can be constructed on a substrate that may also comprise an integrated circuitry component and/or microfluidic mechanisms such as flow controllers. In another embodiment, servo-mechanical components and mechanisms can be used to control the location and movement of the detection element such that the desired signals are detected.

FIGS. 1-14 illustrate various embodiments of the invention.

FIG. 1 illustrates an embodiment of the invention that comprises a fluidic network in association with a magnetic microcoil array, a detection element, an integrated circuitry component, and is in further association with a circuit board. As illustrated, the fluidic network contains a sample zone, a detection zone, and another fluidic zone between the sample zone and the detection zone. The sample is loaded into the sample zone, where analyte present in the sample forms a complex with a magnetic particle. The complex is moved through the fluidic zones to the detection zone by activating the microcoil array. It is then detected in the detection zone by the detection element. The device is further connected with a circuitry component and circuit board, which collects, analyzes, and/or processes signals detected by the detection element.

Figure 2:
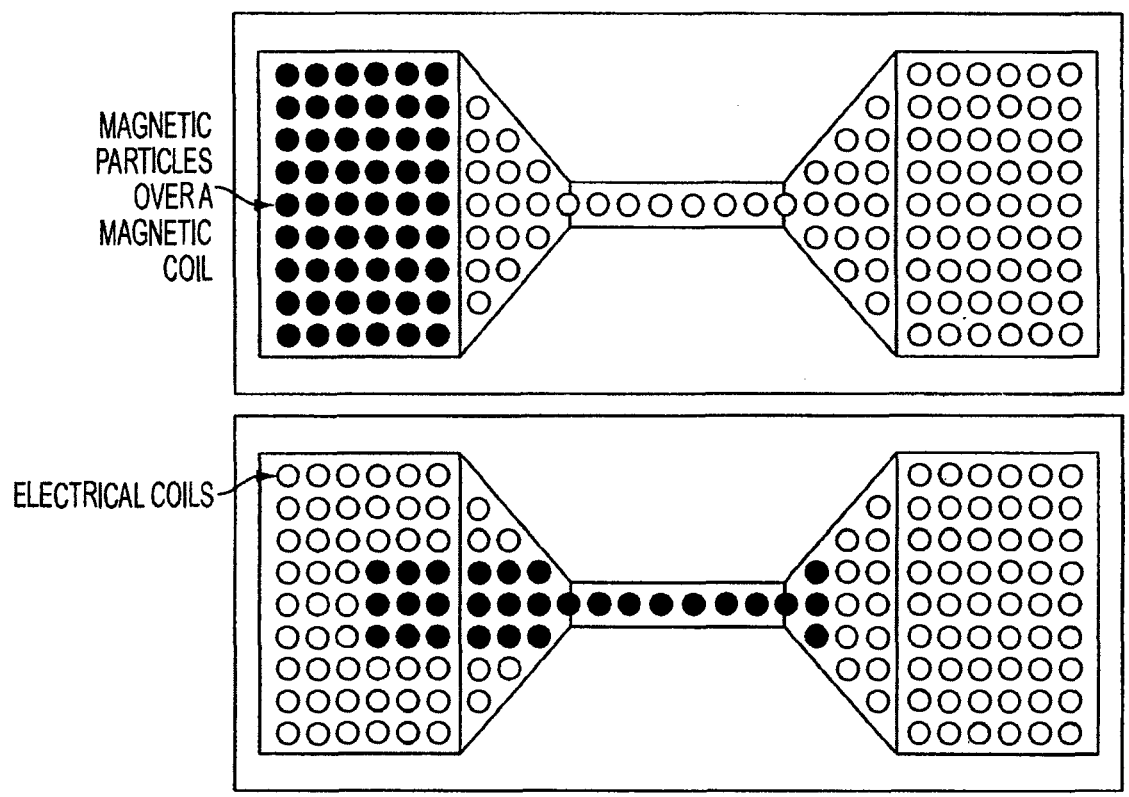
FIG. 2 illustrates an exemplary top-down view of a magnetic microcoil array showing the movement of magnetic particles.

FIG. 2 illustrates magnetic particles overlaying an exemplary magnetic microcoil array, demonstrating the movement of magnetic particles (dark circles) over the magnetic coils. As shown, the microcoils are activated (turned on and off in a directed fashion) to move the magnetic particles from left to right. Molecules that are coupled to the magnetic particles are also moved by activating the microcoils.

Figure 3:
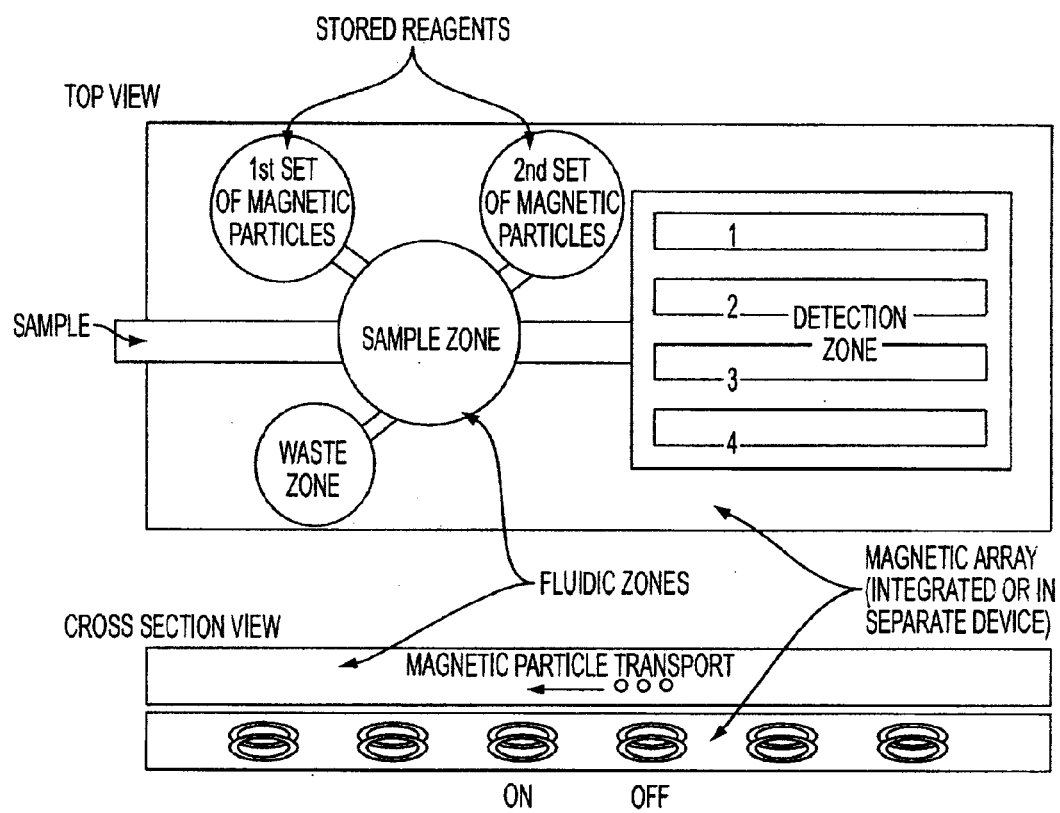
FIG. 3 illustrates a top-down view and cross-section view of the fluidic network.

FIG. 3 illustrates a top-down view and cross-section view of the fluidic network. The cross-section view illustrates the functionally coupled magnetic microcoil array. As shown, the sample is introduced into the sample zone. There are optional fluidic zones for storing reagents, which contain one or more sets of magnetic particles. The underlying magnetic array (which can be integrated or in a separate, coupled device) is activated to move the magnetic particles into the sample zone. In another embodiment (not shown), the magnetic particles are present within the sample zone, and are not located in the storage areas. There is also a waste zone: magnetic particles can be moved into the waste zone and uncomplexed analyte can be left in this area. The magnetic array is activated to move the magnetic particles and complexed analyte into the detection zone. The detection zone can contain one or more different regions (indicated by 1-4) for detection of different analytes.

Figure 4:
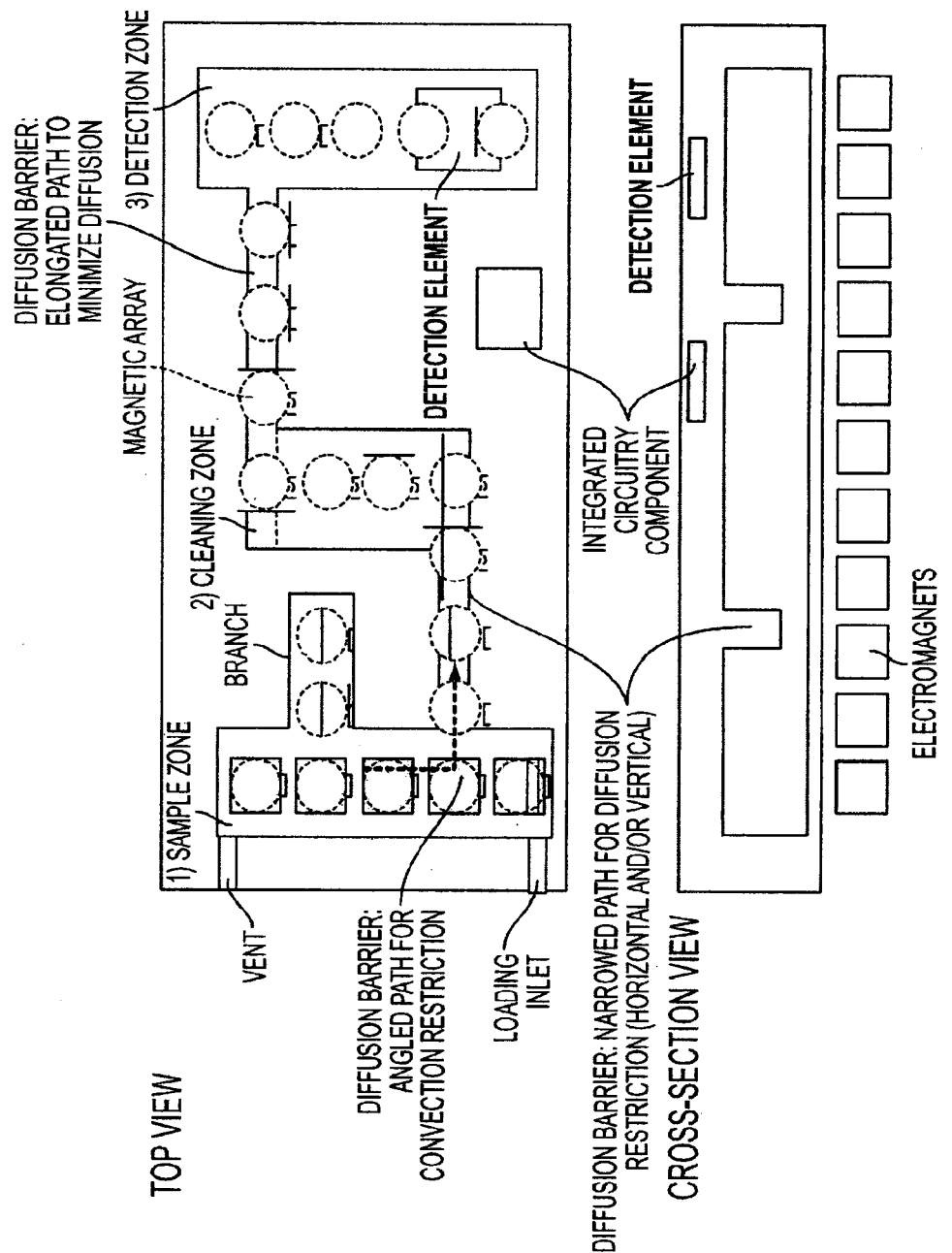
FIG. 4 illustrates a more detailed top-down view and cross-section view of the fluidic network.

FIG. 4 illustrates a more detailed top-down view and cross-section view of the fluidic network functionally coupled to the magnetic microcoil array, providing examples of various diffusion barriers. As shown, the microcoil array is indicated by the dashed ovals in the top-down view, and by the squares in the cross-section view. The sample is inserted into the sample zone through a loading inlet, where it interacts with magnetic particles and the analyte binds to the magnetic particle. The magnetic particles are optionally moved into the branch, which is a fluidic zone containing one or more reagents. The magnetic microcoil array is activated to move the magnetic particles (complexed and uncomplexed) through a diffusion barrier to the cleaning zone. The magnetic particles are further moved into the detection zone, for detection by the detection element. The integrated circuitry component saves data in its memory.

Figure 5:
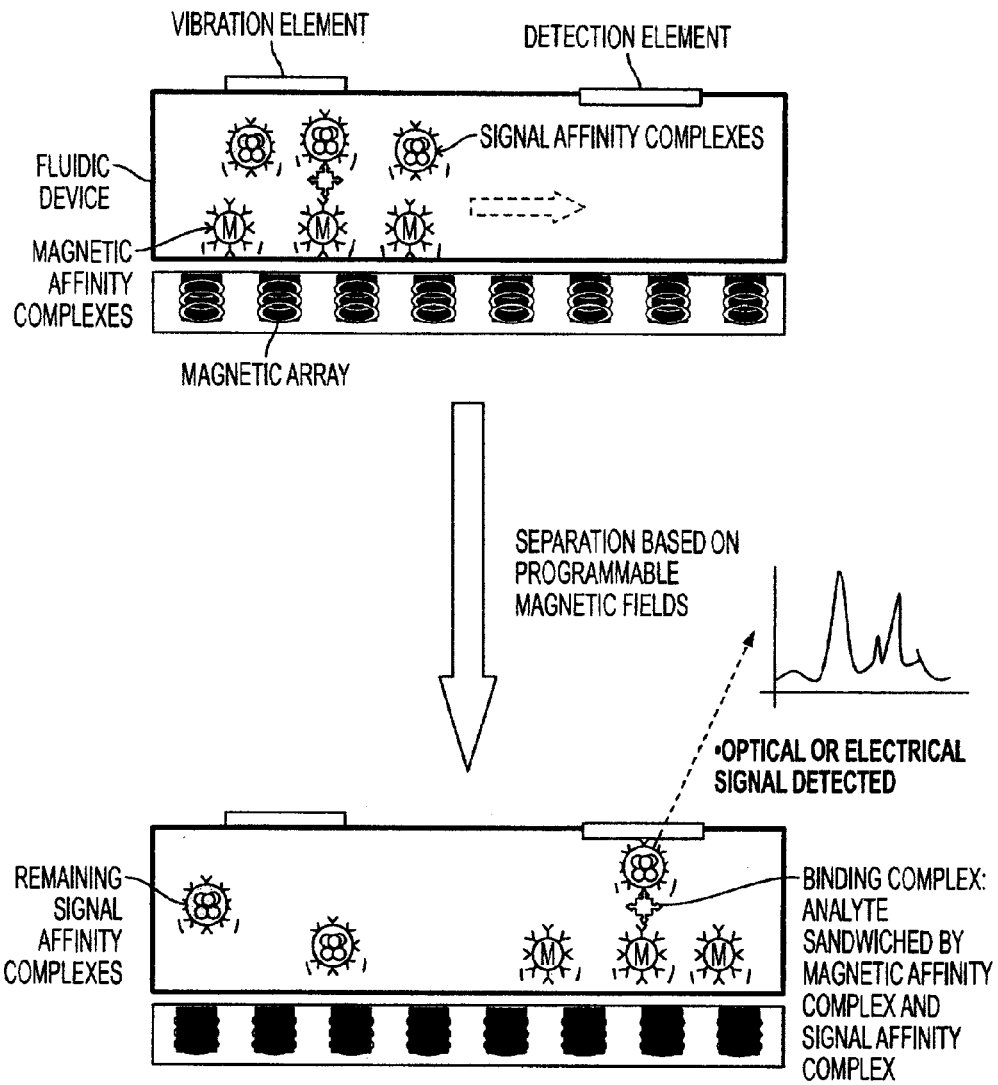
FIG. 5 illustrates a cross-section view of the fluidic network showing the movement of the binding complex to the detection zone.
Figure 6C:
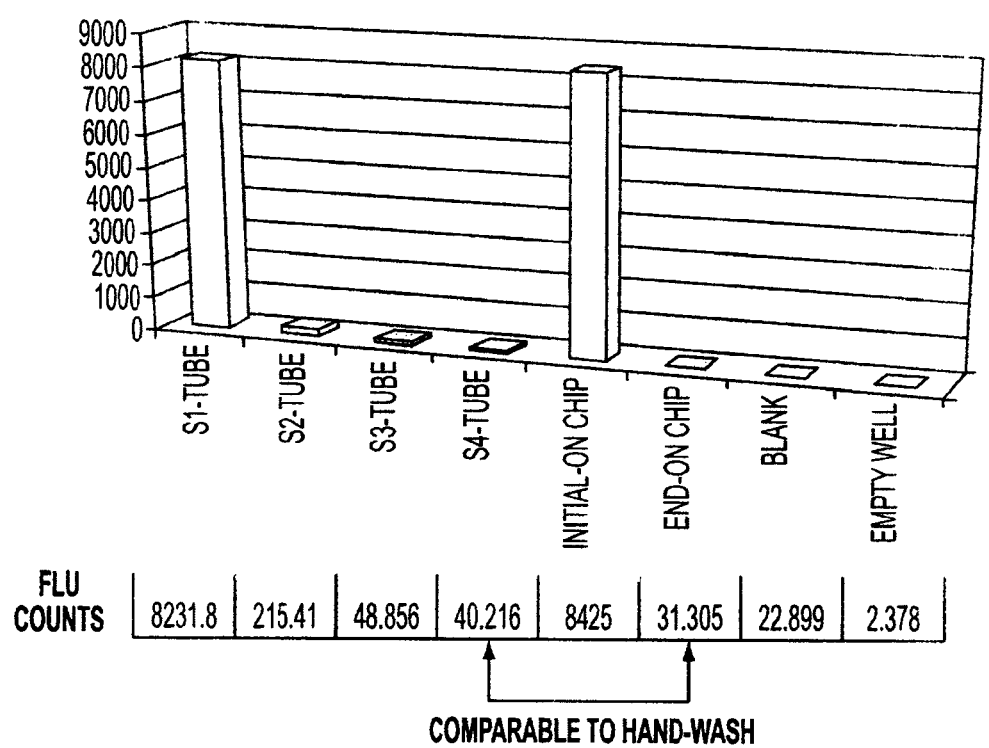
FIG. 6C quantifies the fluorescence of the samples in the tubes from FIG. 6B and samples taken from the fluidic network during FIG. 6A.
Figure 6D:
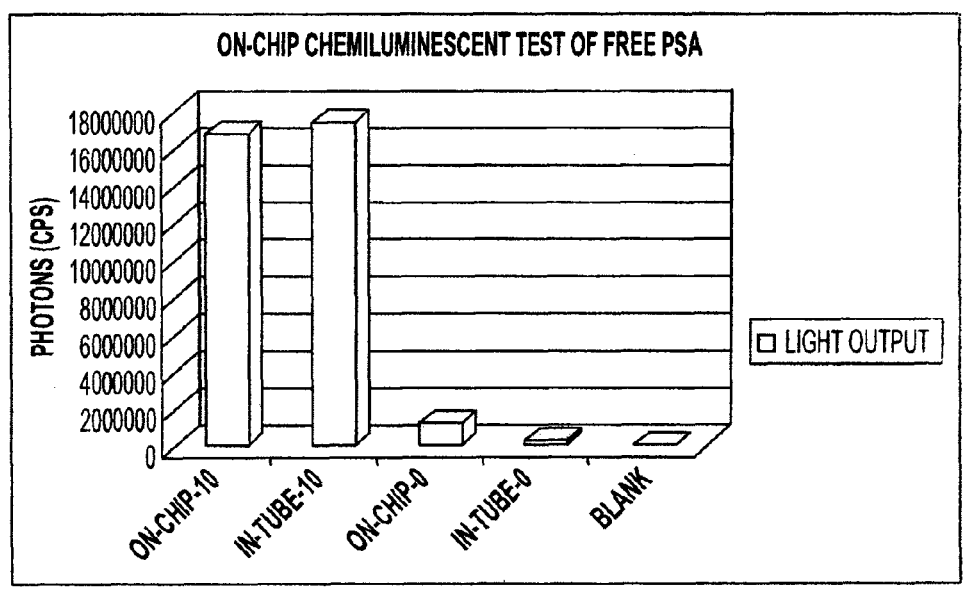
FIG. 6D quantifies on-chip chemiluminescent detection of PSA.

FIG. 5 illustrates a cross-section view of the fluidic network and exemplary method for detecting an analyte. The fluidic network is functionally coupled to the magnetic microcoil array, and contains a magnetic affinity complex, an analyte and a signal affinity complex. The magnetic affinity complex ("M") interacts with the analyte and the signal affinity complex to form a sandwich binding complex. The vibration element is optionally employed to deaggregate the magnetic and signal particles and the analyte, and to allow them to interact. The microcoil array is activated to move the magnetic affinity complexes to the detection zone. Unbound signal affinity complex is not moved to the detection zone. While both complexed and uncomplexed magnetic particles are in the detection zone, the signal is generated only by the signal particles that have interacted with the analyte and the magnetic affinity complex. Both optical and electrical signals can be detected. The signal indicates the presence of the analyte. FIG. 6A illustrates the use of the fluidic network such as a biochip. Magnetic particles and Qdots were loaded into the fluidic network. The magnetic microcoils were activated and the magnetic particles (indicated by the arrows) moved from the sample zone in panel 1 through the fluidic channels and into the detection zone by panel 6. Note that in panel 3, the magnetic microcoils were activated to spread out the magnetic particles. The fluorescent images illustrate that the Qdots did not move from the sample zone. FIG. 6B illustrates the fluorescence of a mixture of magnetic particles and Qdots. As the mixture is washed, it loses fluorescence. FIG. 6C quantifies the fluorescence of the samples in the tubes from FIG. 6B (S1 tube is the original sample, while S2-S4 tubes are the washes) or samples taken from the fluidic network during FIG. 6A ("initial-on chip" indicates the sample zone after the magnetic particles have been moved, while "end-on chip" indicates the sample from the detection zone"). FIG. 6D illustrates on-chip chemiluminescent detection of PSA. Comparative studies were carried out by dividing samples into two-halves, one half for on-chip test and the other for in-tube test. The on-chip test demonstrated the capability of removing signaling particles from sandwich complex by magnetic transport. FIG. 6D quantifies chemiluminescence photo counts corresponding to the analyte, free PSA, for the "on-chip" experiment performed with fluidic network as well as for the "in-tube" (multi-steps) experiment. The on-chip test showed very comparative results to the in-tube test.

Figure 7:
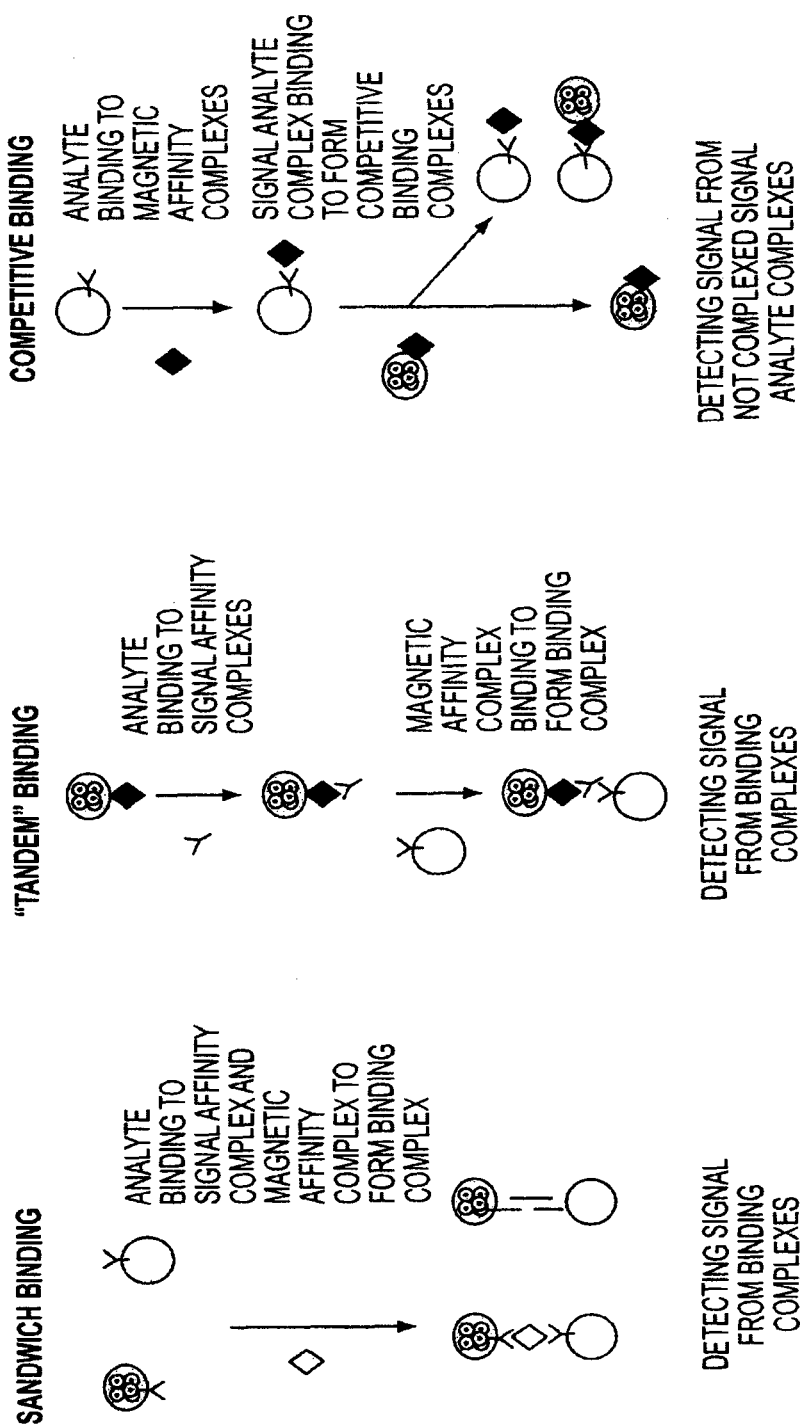
FIG. 7 illustrates the formation of sandwich binding complexes ("sandwich binding" and "tandem binding") and a competitive binding complex.

FIG. 7 illustrates the formation of sandwich binding complexes ("sandwich binding" and "tandem binding") and a competitive binding complex. A sandwich binding complex is formed through the analyte binding to a signal affinity complex and a magnetic affinity complex. The "sandwich binding" shows an example where the analyte is a protein or nucleic acid, while the "tandem binding" shows an example where the analyte is an antibody. An optical or electrical signal is detected from the binding complex. A competitive binding complex is formed when a signal analyte complex displaces the analyte from a magnetic binding complex (analyte plus magnetic affinity complex). Signal is detected from the signal analyte complex that does not form the competitive binding complex.

Figure 8:
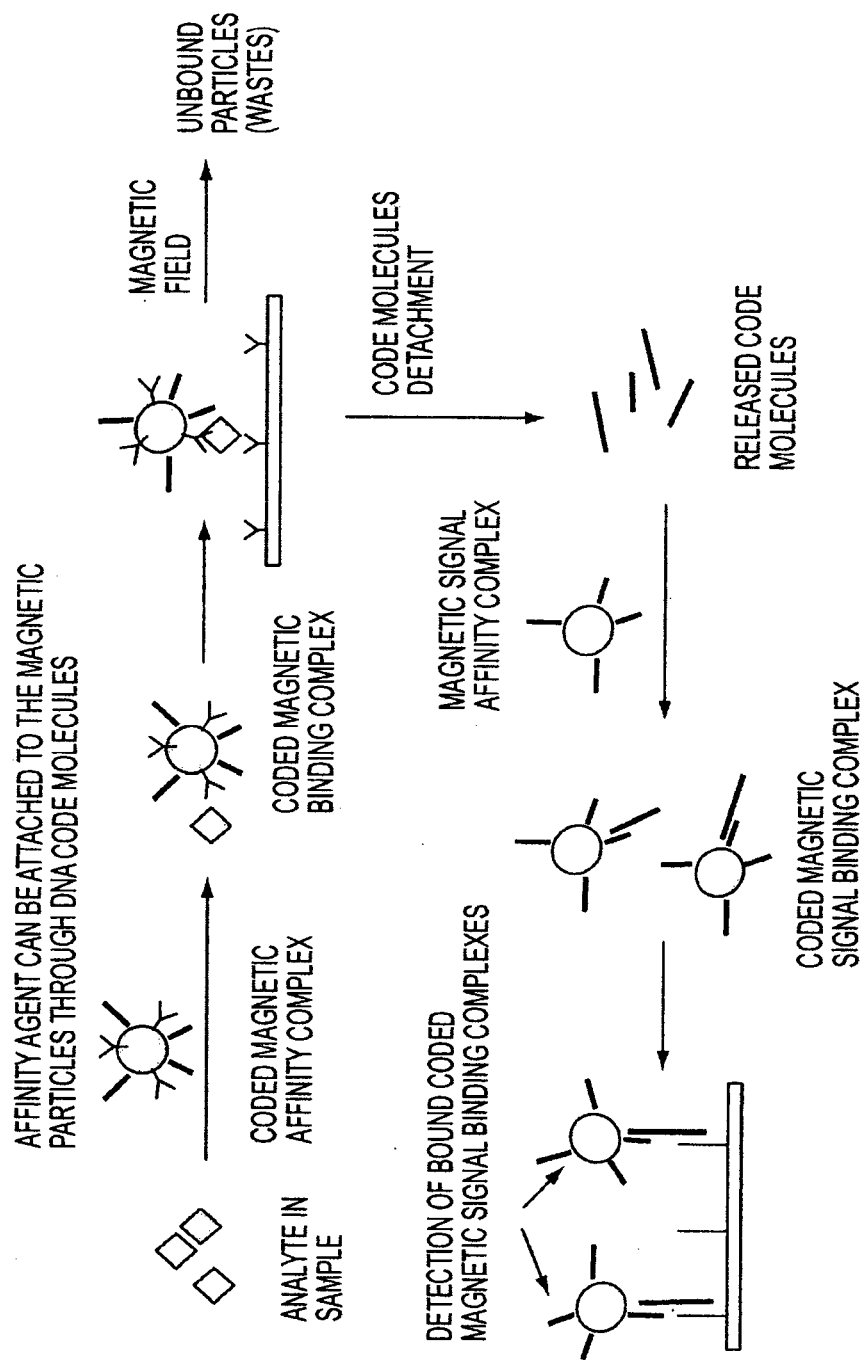
FIG. 8 illustrates the use of codes with a magnetic affinity complex and a magnetic signal affinity complex.

FIG. 8 illustrates the use of codes with a magnetic affinity complex and a magnetic signal affinity complex. The coded magnetic affinity complex comprises a code, an affinity agent and a magnetic particle. It can interact with the analyte to form a coded magnetic binding complex. The microcoil array is activated to move the coded magnetic binding complex to a first affinity surface, where it is bound and immobilized. In this example, the affinity agent on the first affinity surface is complementary to and binds to the affinity agent on the magnetic particle. The code is then detached from the coded magnetic binding complex. The detached code then binds to a magnetic signal affinity complex to form a coded magnetic signal binding complex. Typically the affinity agent of the magnetic signal affinity complex is complementary to the code. In this example, the affinity agent of the magnetic signal affinity complex is a polynucleotide complementary to the code polynucleotide. The microcoil array is activated to move the coded magnetic signal binding complex to one or multiple detection zones comprising a second affinity surface. Typically different areas of the detection zone or the different detection zones contain unique affinity agents to the codes. The affinity agents of the second affinity surface are complementary to and bind the code. The detection element then detects the coded magnetic signal binding complex in the detection zone using electrical sensing methods, optical sensing methods, or enzymatic methods, such as amplifying the affinity agent (if it is a polynucleotide) on the magnetic signal affinity complex.

Figure 9:
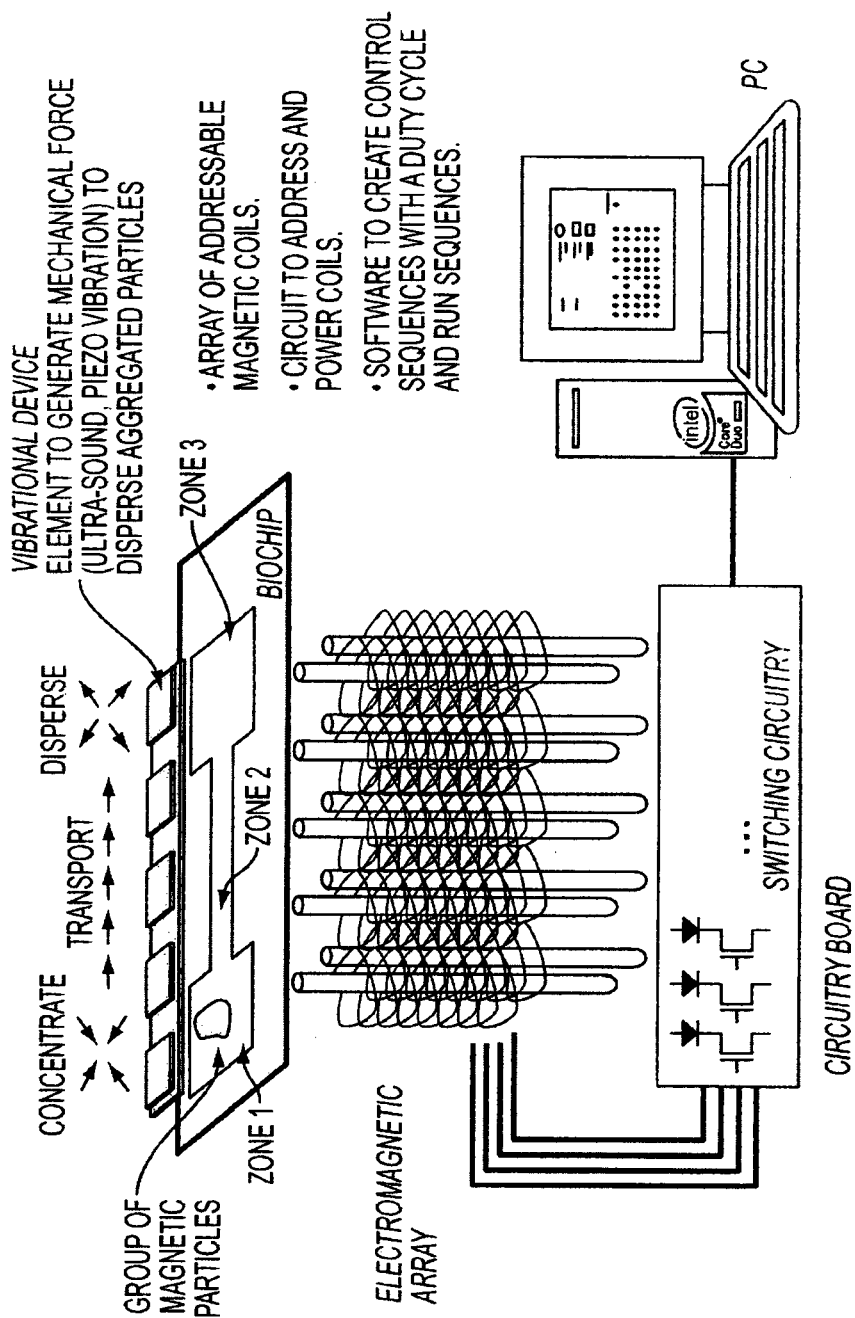
FIG. 9 illustrates an embodiment of the particle (or molecule) transport device of the invention, showing major components which are (1) a fluidic network, e.g., a biochip, (2) an electromagnetic array, (3) a circuitry board; and (4) computer.

FIG. 9 illustrates an embodiment of the particle (or molecule) transport device of the invention, showing major components which are (1) a fluidic network, e.g., a biochip, (2) an electromagnetic array, (3) a circuitry board; and (4) computer. The fluidic network comprises a plurality of fluidic zones, each fluidic zone being connected to the adjacent zone by a diffusion barrier, and an integrated circuitry component, and optionally has a vibration element functionally coupled to the fluidic network. The array of magnetic microcoils functionally is coupled to the fluidic network, wherein the microcoils are programmably activatable to generate a magnetic field in proximity to each microcoil. The electromagnetic array can concentrate or transport magnetic particles, but dispersion of magnetic particles is preferably done by the vibrational device, which could be integrated in the fluidic network. A detection element (not shown in FIG. 9) could be functionally coupled to the fluidic network.

The circuitry board shown in FIG. 9 contains the circuitry to control the elements (core/coil) of the electromagnetic array. The circuitry board is connected, either hard-wired or by wireless connection, to a computer or any other device for controlling the switches of the circuitry board in a preferred sequence. The computer or any processing unit could include an embedded computer processor and/or could be capable of integrated computing.

Particle transport in the fluidic device is achieved by using the magnetic array and magnetic particles. Magnetic particles are commercially available. For clinical diagnostic applications, the particles could be conjugated with affinity binding partners (e.g. nucleic acid probes or antibodies); they could also be used together with other nanoparticles which can serve as either signal source or as carriers of signal sources. Magnetic particles and other reagents are placed in the fluidic device (e.g., biochip) containing multiple zones wherein liquid transport is not needed, and thus mechanism to generate fluid movement force is avoided.

To facilitate biomolecule detection, aggregated or concentrated particles in the fluidic zones may need to be dispersed, mixed, or resuspended in solution locally within in a fluidic zone. Dispersing can be achieved by mechanical means, e.g., the vibrational device such as ultrasounds (acoustic), piezo vibrations. The dispersing elements can be functionally coupled to the nBMA device (integrated with chip or the control device).

Figure 10:
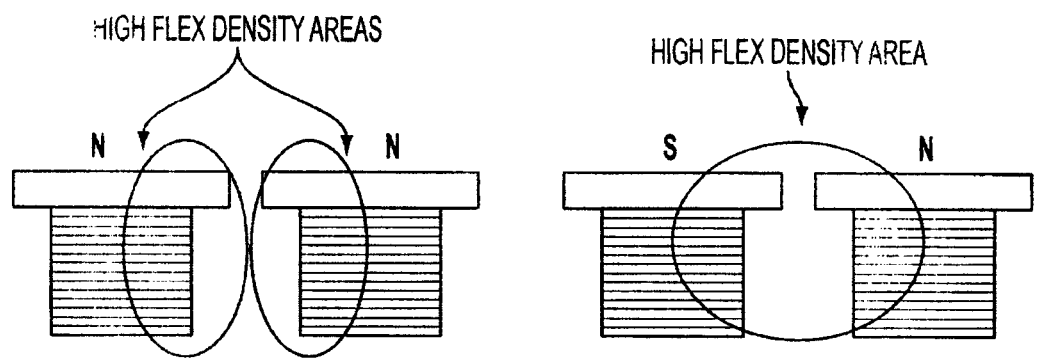
FIG. 10 illustrates electromagnetic coils of the array, showing reversible magnetic polarities, magnetic field gradients (flux) controlled by current flow directions and strength, and flux distributions that can be optimized by varying geometry (shapes) of the heads of the cores.
Figure 10:
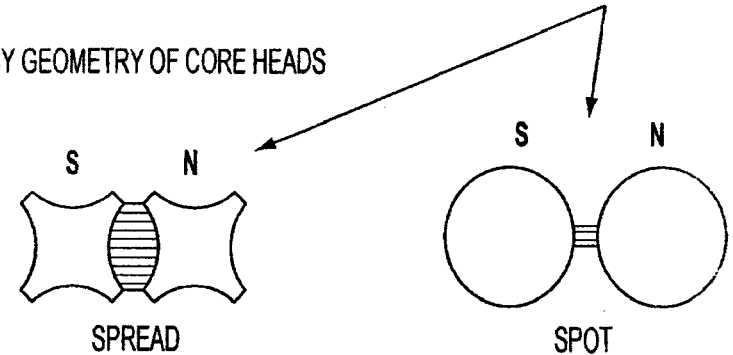

In one embodiment, the electromagnetic array comprises magnetic core, e.g., Fe cores, surrounded by power coils, preferably a set of planar coils. As shown in FIG. 10, the cross sectional areas of the core of the electromagnet could have various geometries such as a star (FIG. 10, bottom left) or a circle (FIG. 10, bottom right). Generally, cores having the star cross-section produce a more even magnetic filed between two adjacent cores while cores having the circular shape produce a concentrated magnetic field in the region where two adjacent cores are closest. Thus, by appropriate choice of the cross-sectional areas of the cores, the electromagnetic array could have regions with substantially uniform or concentrated magnetic field.

The electromagnetic array creates magnetic field gradients that are sufficient to transport the magnetic particles in the fluidic device. The power coils can be switched by the switching circuitry, which in turn can be controlled by a computer. The switching could be on/off, high/low and/or at a desired frequency, which can be determined as a function of the time necessary for a magnetic particle to be transported within the fluidic device.

Figure 11A:
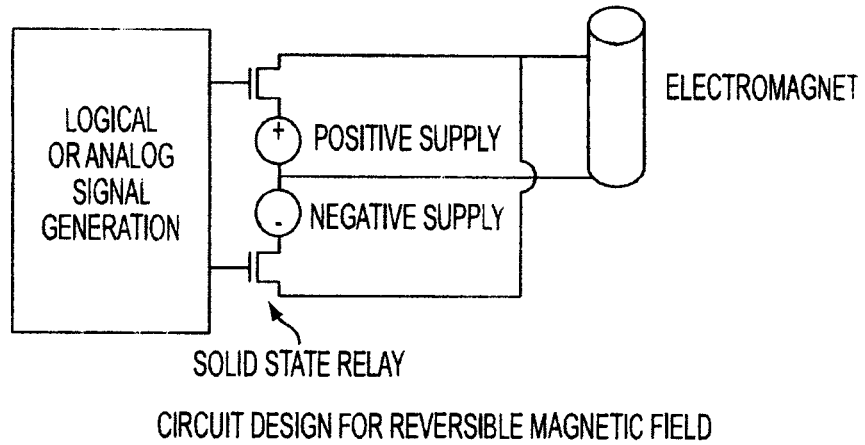
FIGS. 11A and B illustrate a power delivery system, showing an example of ways to minimize the number of power switches.
Figure 11B:
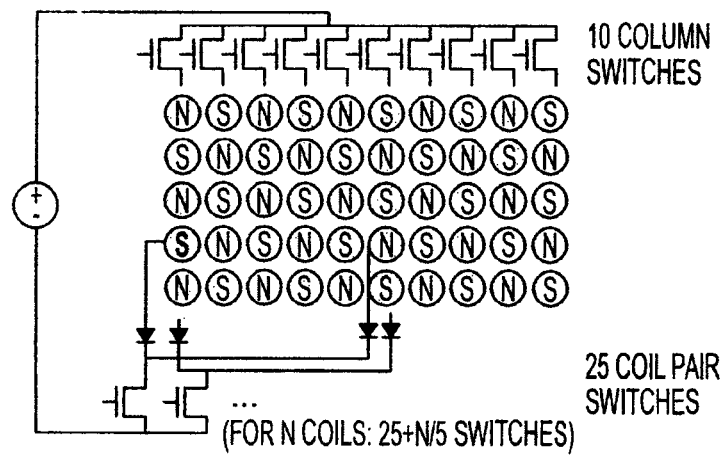

FIGS. 11A and B show an embodiment of the switching circuitry. The computer generates low current signals which are used to control the high current needed for the electromagnets. The current for each coil can be controlled by either a solid state or electromechanical relay or current amplifier which is driven by a logical or analog signal generated by the computer control. FIG. 11A is an example of a circuit for an individual magnetic element for which the polarity can be switched. So one would need two switches per element of the magnetic array. However, by the switching circuitry of FIG. 11B, it would be possible to minimize the number of switches but keep the polarity fixed such that, for example, for N elements containing N coils, one would need just 25+N/5 switches.

Figure 12:
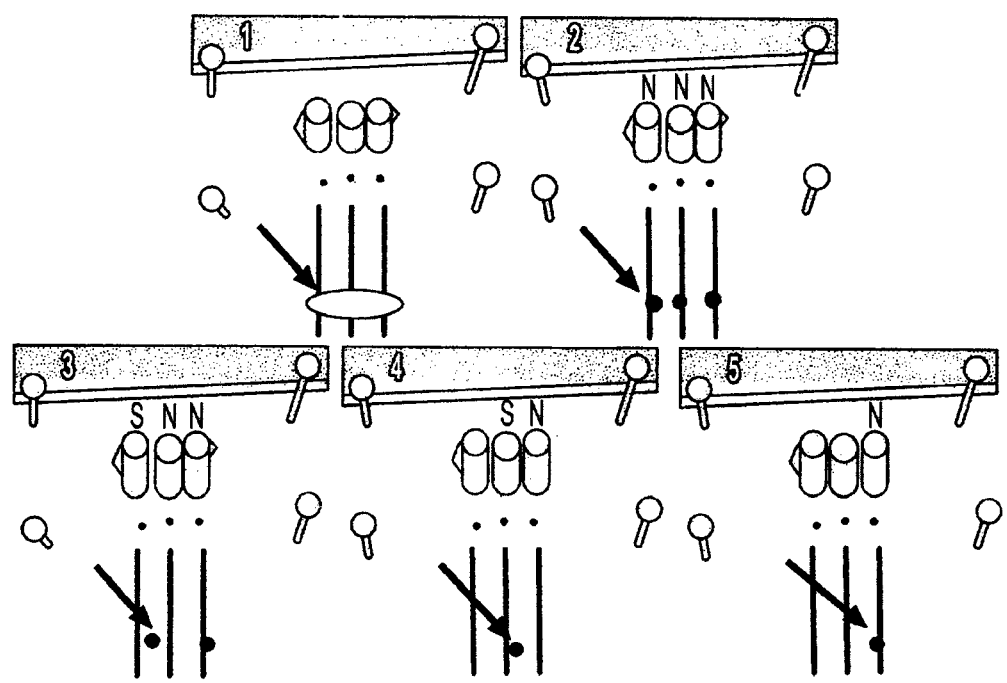
FIG. 12 illustrates an experiment demonstrating magnetic particle concentrating, transporting by varying magnetic fields.

FIG. 12 illustrates an example of the movement of magnetic particles on a microscope slide. Initially, in FIG. 12 (1), a liquid solution containing colored magnetic particles was spread out on a portion of the slide overlaying directly above three core/coil elements. Note that the microscope slide in FIG. 12 has been moved down to take the picture, but in the experiment, the liquid solution was on top of the three core/coil elements. Next, all three elements were switched on to have north (N) polarity. As a result, as illustrated in FIG. 12 (2), the magnetic particles in the liquid solution separated into two distinct regions above the first and third core/coil elements. Next, the three elements were switched on to have south (S), N, N polarity. In this case, as illustrated in FIG. 12 (3), the majority of the magnetic particles moved to a spot between S and N polarity elements and some magnetic particles formed a spot above the third element having N polarity. Next, the three elements were switched to have zero (no), S, N polarity. In this case, as illustrated in FIG. 12 (4), the magnetic particles moved to a spot between the second and third elements having S and N polarity. Finally, the three elements were switched on to have zero, zero and N polarity. In this case, as illustrated in FIG. 12 (5), the magnetic particles moved to a spot above the third element having N polarity. This example clearly demonstrates that a magnetic array within the embodiments of the invention can transport and/or concentrate magnetic particles within a fluid without any external fluid transport mechanism that generates hydraulic pressure for fluid transport.

Figure 13:
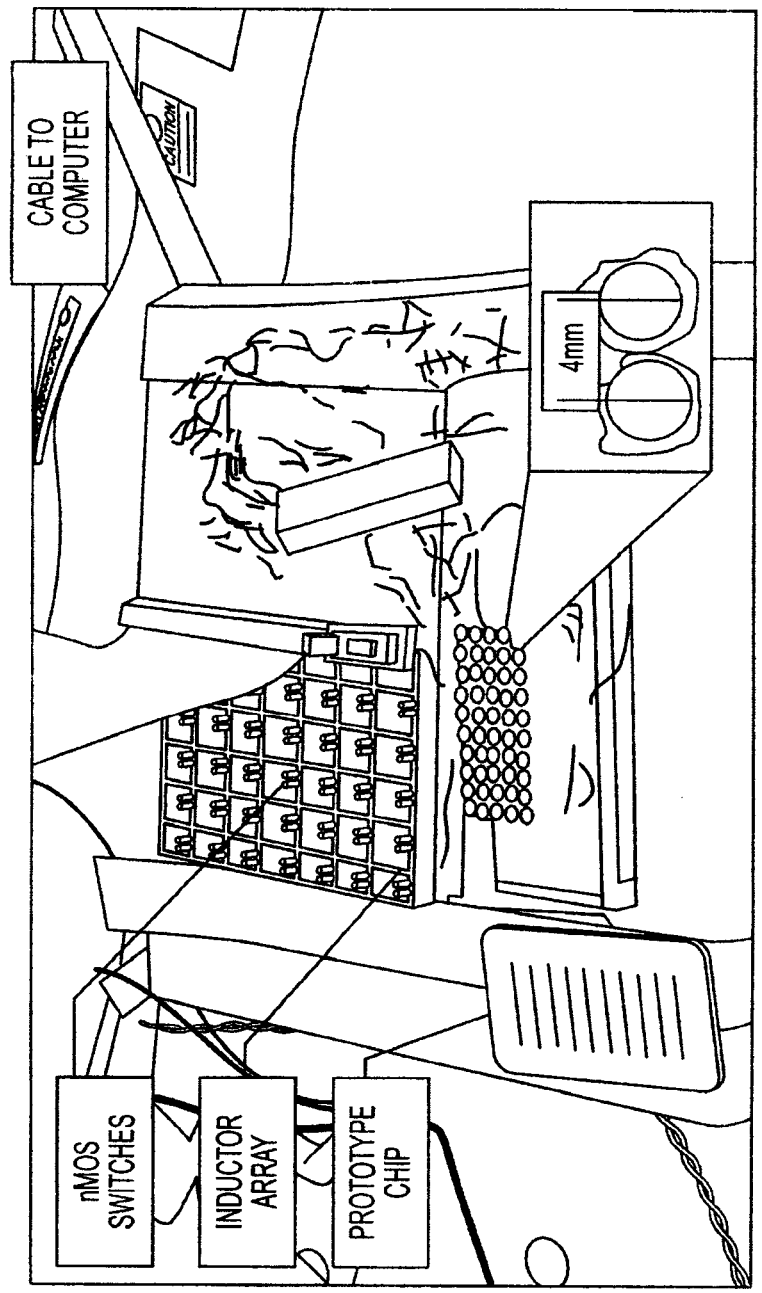
FIG. 13 illustrates a prototype system, showing the coil (inductor) array, switches and other electronic control elements, together with a prototype fluidic chip (biochip).

FIG. 13 shows a prototype system for transport of magnetic particles, the system comprising coil (inductor) array, switches and other electronic control elements, together with a prototype fluidic device (e.g., biochip). The prototype system of FIG. 13 was used to demonstrate transport of magnetic particles in the biochip, illustrated in FIG. 6. FIGS. 6 and 12 illustrate that the transport and/or concentration of magnetic particles demonstrated in FIG. 9 for a three coil array is scalable for any number coils.

FIG. 14 shows the specification for an embodiment of the prototype system of FIG. 13, indicating the magnetic coil structure and magnetic field strengths relative to the coil head surface. As one would recognize, the magnetic field strengths would depend on the spacing of the coils, and the spacing could be varied in different electromagnetic arrays.

Embodiments of the invention are directed to devices and methods for detecting the presence of an analyte in a sample. According to one embodiment, the device comprises a fluidic network comprising a plurality of fluidic zones, each fluidic zone being connected to the adjacent zone by a diffusion barrier, and an integrated circuitry component. According to another embodiment, the invention encompasses a device comprising a substrate containing a plurality of fluidic zones, each fluidic zone being connected to the adjacent fluidic zone by a diffusion barrier, wherein each fluidic zone comprises a fluid, and wherein one or more fluidic zones comprises a magnetic particle. In one aspect, the device is adapted to permit transport of the magnetic particle from one fluidic zone to an adjacent fluidic zone substantially without moving the fluid between the fluidic zones.

An array of magnetic microcoils can be functionally coupled to the fluidic network, which is programmably activatable to generate a magnetic field in proximity to each microcoil. The microcoil array can be integrated into the network, or it can be located near the fluidic zones of the device, so that at least one microcoil is placed suitably for generating a magnetic field in at least a portion of a fluidic zone. A detection element is also functionally coupled to the fluidic network; it can be integrated into the network or located in proximity to the network. Generally, it is situated so that whether integrated or temporarily coupled, it detects optical or electrical signals from one or more of the fluidic zones. A vibration element can also be functionally coupled to the network; it can be integrated into the network or located in proximity to one or more fluidic zones. Typically, when activated, the vibration element is so situated that it will achieve the desired effect of shaking or agitating fluid within one or more fluidic zones of the device.

Certain embodiments of the invention are self-contained such that substantially no liquid flows between the fluidic zones, thereby eliminating the need for flow controllers. In such embodiments, the magnetic particles and any molecules bound to the magnetic particles are moved through the liquid contained within the fluidic zones by activating the magnetic microcoils, and are not moved by the flow of the liquid. Typically in these embodiments, the fluid is present in the fluidic zones to act as a suspending agent. Other embodiments of the invention comprise a flow controller for coordinating liquid flow through the fluidic zones of the device. In such embodiments, the magnetic particles and any molecules bound to the magnetic particles are moved through the fluidic zones by activating the magnetic microcoils and/or also can be moved by activating the flow controller to move the liquid itself. The flow controller is functionally coupled to the network: it can be integrated into the network or external to the network.

The fluidic zones of the device typically comprise a reservoir, channel, groove, opening, or conduit in the substrate of the fluidic device, which is configured for containing a liquid and optionally for containing reagents. In one embodiment, the plurality of fluidic zones comprises a sample zone, a cleaning zone and/or a detection zone. In a further embodiment, it comprises more than one sample zone, cleaning zone, and/or detection zone. It can comprise additional fluidic zones for storing reagents, which can be branches of any of the aforementioned zones. In one embodiment, multiple fluidic zones are contained in parallel within the same device, thus allowing for analysis of multiple samples or multiple analytes in parallel. Each fluidic zone is separated from the adjacent fluidic zone by a diffusion barrier.

Diffusion barriers connect the fluidic zones of the device. They are designed and situated to minimize diffusion or convectance of the contents of one fluidic zone to the next fluidic zone, such that the majority of the contents that move from one zone to the next fluidic zone are moved by directed fluidic flow and/or by activating the magnetic microcoil array. In certain embodiments, the diffusion barrier is a fluidic channel that is designed to alter the path of the fluidic zone. In other embodiments, the diffusion barrier is a thermally-sensitive barrier. Hydrophilic fluid or liquid can be contained in a shape of droplets surrounded by hydrophobic liquid such as silicone oils to form strong diffusion barriers through hydrophilic-hydrophobic interactions so that droplets can be separated and transported without mixing with other fluids as demonstrated in J. Micromech. Microeng. (2006) 16:1875 and Sensors and Actuators B (2006) 113: 563. A diffusion barrier can be accomplished by "particle trapping and transport" through DEP (dielectrophoresis) as demonstrated in Biophysical Journal (1998) 74:1024 and Sensors and Actuators A 121 (2005) 59.

The detection element is situated in proximity to the detection zone. The detection element can be an optical detection element or an electrical detection element. In certain embodiments, the optical detection element is selected from a Raman detector, a photon multiplier tube, a fluorescent reader, or an electrochemical sensor and the electrical detection element is selected from a FET element, a capacity detection element, a current sensor, and a charge sensor. Typically, the detection of the binding complex or the signal analyte complex indicates the presence of the analyte.

In further embodiments, the detection zone comprises a reaction substrate that interacts with a catalytic element to form a fluorogenic, chemiluminescent, or chromogenic product. Non-limiting examples of reaction substrates include Lumigen APS-5, Lumigen TMA-6, Lumigen PS-atto, Lumigen PS-3, $H_2O_2$ with an oxidizable compound, Amplex Red, 3,5,3',5'-tetramethylbenzidine (TMB), glucose, $O_2$, ATP, $Mg^{2+}$, luciferin, inoluciferin, quinolinyl, coelentrazine, aldehyde, $FMNH_2$, and analogs and combinations thereof.

Typically, if the detection zone comprises a reaction substrate, the magnetic particle and/or the signal particle comprises a catalytic element that serves as an agent to cause a chemical reaction to occur in the reaction substrate, where the reaction product is detectable by the detection element. In certain non-limiting embodiments, the catalytic element is selected from the group consisting of alkaline phosphatase, horseradish peroxidase, glucose oxidase, luciferase (from firefly, *Renilla*, bacteria, or other sources) or analogs or combinations thereof. The catalytic element can be covalently or non-covalently conjugated to the signal particle through a functionalized polymer. The fluidic zones of the device generally contain an appropriate buffer to permit the reaction to occur.

The sample zone of the device comprises a magnetic particle selected from the group consisting of a magnetic affinity complex and a coded magnetic affinity complex. Magnetic particles may also be present within other fluidic zones of the device. The microcoils are activated in such a manner as to move the magnetic particles within the device.

The sample zone or other zone of the device can also comprise a signal particle selected from the group consisting of signal affinity complexes, signal analyte complexes, and coded magnetic signal affinity complexes, among others. In certain embodiments the signal particle is a SERS-active nanoparticle, a fluorescent nanoparticle, a nanoparticle coupled to a surface-enhanced fluorescent tag, or a core nanoparticle covalently coupled to a catalytic element. In one embodiment, the signal particle is a COIN particle. In other embodiments, the signal particle is a Qdot, or another fluorescent nanoparticle, such as SEF nanoparticle or a FluoDot. In further embodiments, the signal particle is any nanoparticle (i.e. gold, silver, CdS, CdSe, copper, $Eu^{3+}$-coated polymer, an organic polymer (homo or hetero), an inorganic compound, or composite compounds, etc.). Additionally, the SERS-active nanoparticle and fluorescent nanoparticle can also be functionally coupled to a catalytic element. In certain embodiments, the sample zone of the fluidic device comprises the signal particle. Alternatively, the sample particle is contained within another fluidic zone. In further embodiments, different or the same signal particles can be contained within more than one fluidic zone.

Embodiments of the invention also include methods of using the devices to detect the presence of an analyte.

The device contains magnetic particles within one or more fluidic zones, and the microcoil array is activated to thereby move the magnetic particles within that zone or to another zone. In one method, the magnetic particle within the sample zone is a magnetic affinity complex. A sample suspected of comprising an analyte is introduced into the sample zone, wherein the magnetic affinity complex binds to the analyte to form a magnetic binding complex. The microcoil array is activated to move the magnetic binding complex from the sample zone to another fluidic zone.

In another embodiment, the magnetic particle is a magnetic signal affinity complex. A sample suspected of comprising an analyte is introduced into the sample zone, wherein the magnetic signal affinity complex binds to the analyte to form a magnetic signal binding complex. The microcoil array is activated to move the magnetic signal binding complex from the sample zone to another fluidic zone. It is then detected by the detection element, indicating the presence of the analyte.

In another embodiment, one or more fluidic zones also comprise a signal affinity complex. The analyte is combined with the magnetic affinity complex and the signal affinity complex, either simultaneously or sequentially, where the magnetic affinity complex and the signal affinity complex bind to the analyte to form a sandwich binding complex. The microcoil array is activated to move the sandwich binding complex to the detection zone of the fluidic network, where it is detected by the detection element, and where the detection of the sandwich binding complex indicates the presence of the analyte. In such an embodiment, the analyte is typically a protein, an antibody, or a nucleic acid.

In a further embodiment, the sample zone comprises a magnetic affinity complex, and one or more fluidic zones comprise a signal analyte complex. The magnetic affinity complex binds to the analyte in the sample to form a magnetic binding complex. Optionally, the microcoil array is activated to move the magnetic binding complex to another fluidic zone. The signal analyte complex then displaces the analyte from the magnetic binding complex to form a competitive binding complex. Optionally, the microcoil array is activated to move the competitive binding complex to another fluidic zone. The detection element detects an optical or electrical signal from the signal analyte complex that did not form the competitive binding complex, thus indicating the presence of the analyte. In such an embodiment, the analyte is typically a small molecule such as, but not limited to, sugars, drugs, steroids, and vitamins.

In another embodiment, the sample zone comprises a coded magnetic affinity complex. A sample suspected of comprising an analyte is introduced a sample into the sample zone, wherein the coded magnetic affinity complex binds to the analyte to form a coded magnetic binding complex. The microcoil array is activated to move the coded magnetic binding complex from the sample zone to a first affinity surface where it is immobilized. Typically, the affinity agent of the first affinity surface binds to the analyte or to the affinity agent coupled to the magnetic particle. The code is detached from the bound coded magnetic binding complex. A magnetic signal affinity complex is provided in one of the fluidic zones, so situated that the detached code binds to the magnetic signal affinity complex to form a coded magnetic signal binding complex. Typically, the affinity agent of the magnetic signal affinity complex is a polynucleotide complementary to the code. The microcoil array is activated to move the coded magnetic signal binding complex to the detection zone which comprises a second affinity surface, where it is immobilized. Typically, an affinity agent of the second affinity surface comprises a polynucleotide complementary to the code. The coded magnetic signal binding complex is then detected by the detection element. The second affinity surface can comprise an array of probes for detecting any number of analytes.

The vibration element can be activated to agitate the fluid of one or more of the fluidic zones. In certain embodiments, the vibration element agitates the fluid in one or more fluidic zones to disperse the magnetic particles, analyte, and/or signal particles so that they can interact to form a binding complex. In other embodiments, the vibration element agitates the fluid in one or more fluidic zones to facilitate aggregation-disaggregation and removal of unbound signal particles and/or non-analyte components of the sample from the binding complex. For example, before the binding complex is moved to the detection zone, it is moved to the cleaning zone where the vibration element is activated to aggregate and de-aggregate the binding complex to remove unbound signal particles and/or other components from the sample from the binding complex. In other embodiments, a coded magnetic binding complex and/or a coded signal binding complex are moved to a cleaning zone by activating the microcoil array, wherein the vibration element is activated to aggregate and de-aggregate the complexes to thereby remove unbound coded magnetic affinity complex, detached code, and/or magnetic signal affinity complex before the binding complex is moved to the next zone.

Embodiments of the invention also comprise methods of fabricating the devices. One embodiment comprises fabricating a plurality of fluidic zones on a substrate, where at least one of the fluidic zones is a sample zone designed to hold a sample and a magnetic particle, fabricating one or more diffusion barriers on the substrate, wherein a diffusion barrier connects each fluidic zone to the adjacent fluidic zone; and forming an integrated circuitry component for storing data on the substrate. The diffusion barrier can be fabricated as a fluidic channel or as a thermally-sensitive barrier. In further embodiments, a microcoil array is fabricated on the substrate. Alternatively, the microcoil array is fabricated separately, and is removeably coupled to the device when it is in use. A detection element can be fabricated into the substrate, or can be fabricated separately and removeably coupled to the device when in use. Preferably the detection element is an optical detection element or an electrical detection element. In further embodiments, a vibration element is fabricated into the device. Alternatively, the vibration element is fabricated separately and removeably coupled to the device when in use.

In certain embodiments, fabricating the plurality of fluidic zones on a substrate comprises combining two or more solid supports.

Embodiments of the invention also comprise a binding complex, which is an analyte bound to a magnetic affinity complex and a signal affinity complex. Typically the analyte is a protein, an antibody or a nucleic acid. In one embodiment, the analyte comprises an anti-PSA antibody. In a further embodiment, the signal affinity complex comprises a COIN-PSA conjugate. The magnetic affinity complex can comprise a streptavidin-coated magnetic bead. The analyte can comprise an antibody, which includes an autoantibody.

As disclosed herein, compound and molecules suitable for analysis by the embodiments of the invention include proteins, peptides, and, specifically, nucleic acids (DNA and RNA), which can form double-stranded molecules by hybridization, that is, complementary base pairing. For example, in an embodiment of the invention, a molecular probe, such as a DNA probe, is associated with or attached to a fluidic zone, which is located near or on the surface of, or otherwise integrated into, the substrate. The specificity of nucleic acid hybridization from the binding of the analyte to the molecular probe is such that the detection of molecular and/or nanomaterials binding events can be done through measurements of the signals by the detection element or other external circuitry. This specificity of complementary base pairing also allows thousands of hybridization to be carried out simultaneously in the same experiment on a DNA chip (also called a DNA array).

Molecular probes are immobilized on the surface of individual or individually addressable reservoirs through surface functionalization techniques. The probe in a DNA chip is usually hybridized with a complex RNA or cDNA target (the analyte) generated by making DNA copies of a complex mixture of RNA molecules derived from a particular cell type (source). The composition of such a target reflects the level of individual RNA molecules in the source. The optical or electrical signals resulting from the binding events from the DNA spots of the DNA chip after hybridization between the probe and the target represent the relative expression levels of the genes of the source.

The DNA chip could be used for differential gene expression between samples (e.g., healthy tissue versus diseased tissue) to search for various specific genes (e.g., connected with an infectious agent) or in gene polymorphism and expression analysis. Particularly, the DNA chip could be used to investigate expression of various genes connected with various diseases in order to find causes of these diseases and to enable accurate treatments.

Using embodiments of the invention, one could find a specific segment of a nucleic acid of a gene, i.e., find a site with a particular order of bases in the examined gene. This detection could be performed by using a diagnostic polynucleotide made up of short synthetically assembled single-chained complementary polynucleotides—a chain of bases organized in a mirror order to which the specific segment of the nucleic acid would attach (hybridize) via A-T or G-C base pairing interactions.

The practice of the embodiments of the invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the examples herein below. However, other equivalent conventional procedures can, of course, also be used.

The devices of the embodiments of the invention may be formed by any suitable means of manufacture, including semiconductor manufacturing methods, microforming processes, molding methods, material deposition methods, etc., or any suitable combination of such methods. In certain embodiments one or more of the microcoils, and circuitries may be formed via semiconductor manufacturing methods on a semiconductor substrate. Thin film coatings may be selectively deposited on portions of the substrate surface. Examples of suitable deposition techniques include vacuum sputtering, electron beam deposition, solution deposition, and chemical vapor deposition. The coatings may perform a variety of functions. For example, the coatings may be used to increase the hydrophilicity of a surface or to improve high temperature properties. Conductive coatings may be used to form the microcoils. Coatings may be used to provide a physical barrier on the surface, e.g. to retain fluid at specific sites on the surface.

In one embodiment of the invention, the substrate is made through combining two or more smaller substrates or solid support. Specifically, the fabricating of the fluidic zones, or the fabricating of the microcoils may involve combining two or more smaller substrates to form the substrate.

The substrate used in the embodiments of the invention may comprise various materials including, but not limited to silicon, glass, metal, and polymeric material. According to the embodiments, the substrate comprises an integrated circuit, a microarray, a macroarray, fluidic zones, a detection element, a vibration element, or a combination thereof.

In on embodiment of the invention, the sample zone for holding a sample comprises a reservoir, a channel, an opening, a surface, or a combination thereof. According to another embodiment, the microcoil comprises of copper, aluminum, gold, silver, or a mixture thereof. The microcoil is placed near or adjacent to the fluidic zones.

As disclosed herein, silicon is a suitable material for attaching other materials, such as metal or magnetic materials and forming structures, such as openings and channels coupled with microelectronics or other microelectromechanical systems (MEMS). It also has good stiffness, allowing the formation of fairly rigid microstructures, which can be useful for dimensional stability. In a specific embodiment of the invention, the substrate comprises an integrated circuitry component selected from an integrated circuit (IC), a packaged integrated circuit, and an integrated circuit die. For example, the substrate may be a packaged integrated circuit that comprises a microprocessor, a network processor, or other processing device.

In another embodiment, the method further comprises forming circuitry on or within the detection unit that is capable of amplifying or processing the signals detected by the detection element. The substrate for the detection element may be constructed using, for example, a Controlled Collapse Chip Connection (or "C4") assembly technique, wherein a plurality of leads, or bond pads are internally electrically connected by an array of connection elements (e.g., solder bumps, columns).

According to the embodiments of the invention, microcoils can be fabricated on or within the substrate using a number of techniques, including etching, bonding, annealing, adhering/seeding, lithography, molding, and printing. Physical vapor deposition (PVD) and chemical vapor deposition (CVD) can also be used. In one embodiment, microcoils are fabricated on an oxidized silicon substrate by electroplating metals inside a deep photoresist mold and then passivated using an epoxy based resist.

The substrate of the embodiments of the present invention is suitable for forming openings, voids, surfaces, or microchannels thereon for holding fluid and fluidic communications. The sample zone may be open or closed along. Various methods may be used to form the sample zone on the substrate. For example, a reservoir or an open microchannel can be fabricated on a silicon substrate by etching methods known to those skilled in the art. Closed channels can be formed by sealing the open channels at top using methods such as anodic bonding of glass plates onto the open channels on the silicon substrate.

According to one embodiment of the invention, to fabricate a channel on a silicon substrate, a photoresist (positive or negative) is spun onto the silicon substrate. The photoresist is exposed to UV light through a high-resolution mask with the desired device patterns. After washing off the excessive unpolymerized photoresist, the silicon substrate is placed in a wet chemical etching bath that anisotropically etches the silicon in locations not protected by the photoresist. The result is a silicon substrate in which channels are etched. If desired, a glass cover slip is used to fully enclose the channels. Also, holes are drilled in the glass to allow fluidic access. For straighter edges and a deeper etch depth, deep reactive ion etching (DRIE) can be used as an alternative to wet chemical etching.

In another embodiment of the invention, channels may be formed on a silicon substrate using the following method. A seed layer of a metal, such as copper, is deposited over a surface of the substrate. Any suitable blanket deposition process may be used to deposit the seed layer of metal, such as physical vapor deposition (PVD), chemical vapor deposition (CVD), or other methods known to those skilled in the art. A layer of a sacrificial material, such as a dielectric material or a photoresist material, is then deposited over the seed layer. By removing the sacrificial material, for example using chemical etch process or thermal decomposition process, a number of trenches in the sacrificial layer are formed, and the seed layer is exposed in each of the trenches. Another layer of the metal, such as copper, is deposited over the exposed seed layer in the trenches. The metal layer extends over portions of the upper surface of the sacrificial layer; but gaps remain between the metal material layers extending from adjacent trenches and over the upper surface of the sacrificial layer. The sacrificial layer is removed, for example using chemical etching process or thermal decomposition process, and regions from which the sacrificial layer has been removed form channels in the metal layer. An additional layer of the metal is deposited over the upper surfaces of the metal layer to close the gaps over the channels.

In the embodiments of the invention, reservoirs, openings and channels can be made by using soft lithography method with suitable materials, such as silicon and polydimethylsiloxane (PDMS). With these techniques it is possible to generate patterns with critical dimensions as small as 30 nm. These techniques use transparent, elastomeric PDMS "stamps" with patterned relief on the surface to generate features. The stamps can be prepared by casting prepolymers against masters patterned by conventional lithographic techniques, as well as against other masters of interest. Several different techniques are known collectively as soft lithography. They are as described below:

Near-Field Phase Shift Lithography.

A transparent PDMS phase mask with relief on its surface is placed in conformal contact with a layer of photoresist. Light passing through the stamp is modulated in the near-field. Features with dimensions between 40 and 100 nm are produced in photoresist at each phase edge.

Replica Molding.

A PDMS stamp is cast against a conventionally patterned master. Polyurethane is then molded against the secondary PDMS master. In this way, multiple copies can be made without damaging the original master. The technique can replicate features as small as 30 nm.

Micromolding in Capillaries (MIMIC).

Continuous channels are formed when a PDMS stamp is brought into conformal contact with a solid substrate. Capillary action fills the channels with a polymer precursor. The polymer is cured and the stamp is removed. MIMIC is able to generate features down to 1 μm in size.

Microtransfer Molding ((TM).

A PDMS stamp is filled with a prepolymer or ceramic precursor and placed on a substrate. The material is cured and the stamp is removed. The technique generates features as small as 250 nm and is able to generate multilayer systems.

Solvent-Assisted Microcontact Molding (SAMIM).

A small amount of solvent is spread on a patterned PDMS stamp and the stamp is placed on a polymer, such as photoresist. The solvent swells the polymer and causes it to expand to fill the surface relief of the stamp. Features as small as 60 nm have been produced.

Microcontact Printing ((CP).

An "ink" of alkanethiols is spread on a patterned PDMS stamp. The stamp is then brought into contact with the substrate, which can range from coinage metals to oxide layers. The thiol ink is transferred to the substrate where it forms a self-assembled monolayer that can act as a resist against etching. Features as small as 300 nm have been made in this way.

Techniques used in other groups include micromachining of silicon for microelectromechanical systems, and embossing of thermoplastic with patterned quartz. Unlike conventional lithography, these techniques are able to generate features on both curved and reflective substrates and rapidly pattern large areas. A variety of materials could be patterned using the above techniques, including metals and polymers. The methods complement and extend existing nanolithographic techniques and provide new routes to high-quality patterns and structures with feature sizes of about 30 nm.

Standard lithography on silicone wafer or silica glass could also be used to fabricate the devices of the embodiments of this invention. Reservoirs, openings and channels in the micrometer or nanometer scale can be fabricated from the devices. If fluidic flow is employed, it can be controlled by pressure gradient, electrical field gradient, gravity, and/or heat gradient. The surfaces of the fluidic zones and/or the diffusion barriers can be modified with polymers (polyethylene glycol (PEG)-dramatized compounds) that can minimize non-specific binding. The solid support can be inorganic material (e.g., glass, ceramic) or metal (e.g., aluminum). Biomolecules, proteins, antibodies, and/or nucleic acids can be coated on the surface of the substrate for specific analyte binding.

In the embodiments of the invention, the channels formed on the substrate may be straight or have angles or curves along their lengths. The characteristics and layout of the channels are determined by the specific applications the device is designed for. Although straight channels lining next to one another are a typical design for microfluidic devices, the channels in the embodiments of the invention may be designed in many different patterns to serve specific separation and detection requirements. Specifically, the design of the channels takes into consideration of the microcoils associated with the fluidic zones such that one or more microcoils are capable of generating excitation magnetic fields across at least a portion of one fluidic zones. Further, in the embodiments of the invention, the cross-section of the fluidic zone so formed may be uniform or vary along the channel's length, and may have various shapes, such as rectangle, circle, or polygon.

EXAMPLES

Example 1

Magnetic Particles are Separated from Signal Particles in a Fluidic Device

A biochip was constructed as shown in FIG. 6, containing a sample zone, a cleaning zone and a detection zone, which was functionally coupled to a magnet. A mixture of magnetic particles and Qdot particles was loaded into the sample zone. The arrows indicate the position of the magnetic particles over time, showing that they moved from the sample zone in panel 1 to the detection zone in panel 6. UV fluorescence indicates that the Qdots were still located in the sample zone since no significant fluorescence was detected beyond the sample zone.

Solutions were retrieved from the sample zone and the detection zone, respectively, and finally adjusted to the same volumes for comparison. As a control, the same amount of particle mixture was cleaned in tubes; the supernatant from each step was saved to measure Qdot carry-over in the absence of analyte (see FIG. 6B).

As shown by the control test in tubes (FIG. 6C), Qdots were separated from magnetic particles after 4 washing steps; the same result could be achieved using the test chip; meaning the magnetic particles were free of Qdots after they were transported from the sample zone to the detection zone without liquid exchanges. For example, when PSA was the analyte, as low as 0.1 pg of PSA was detected using SERS technology and COIN particles (FIG. 6D).

The characteristics of some of the embodiments of the invention are illustrated in the Figures and examples, which are intended to be merely exemplary of the invention. This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

We claim:

1. A method comprising providing a device comprising an integrated circuitry component and a fluidic network comprising a magnetic particle in a fluid, generating a magnetic field that interacts with the fluidic network, and transporting the magnetic particle by the magnetic field that interacts with the fluidic network without fluidic movement of the fluid in the fluidic network, wherein generating the magnetic field that interacts with the fluidic network is by programmably activating magnetic microcoils in a vicinity of the fluidic network.

2. The method of claim 1, wherein the magnetic particle comprises a magnetic affinity complex bound to an analyte.

3. The method of claim 1, wherein the magnetic particle comprises a magnetic affinity complex and a signal affinity complex, both bound to different bind sites of an analyte.

4. The method of claim 3, wherein the analyte is a protein, an antibody, or a nucleic acid.

5. The method of claim 1, wherein the magnetic particle comprises a signal affinity complex, bound to an analyte.

6. The method of claim 5, further comprising detecting the analyte bound to the magnetic particle.

7. The method of claim 1, wherein the magnetic particle comprises a coded affinity complex.

8. The method of claim 7, wherein the coded affinity complex is not magnetic.

9. The method of claim 1, further comprising vibrating the fluid.

10. The method of claim 1, wherein transporting the magnetic particle comprises transporting the magnetic particle through a diffusion barrier that is part of the fluidic network.

* * * * *